US006902935B2

(12) United States Patent
Kaufman et al.

(10) Patent No.: US 6,902,935 B2
(45) Date of Patent: Jun. 7, 2005

(54) METHODS OF MONITORING EFFECTS OF CHEMICAL AGENTS ON A SAMPLE

(75) Inventors: Howard Kaufman, Newton, MA (US); Alex Zelenchuk, Stoughton, MA (US); Ross Flewelling, Chelmsford, MA (US); Philippe Schmid, Lausanne (CH); Ze'ev Hed, Nashua, NH (US)

(73) Assignee: MediSpectra, Inc., Lexington, MA (US)

( * ) Notice: Subject to any disclaimer, the term of this patent is extended or adjusted under 35 U.S.C. 154(b) by 962 days.

(21) Appl. No.: 09/738,614

(22) Filed: Dec. 15, 2000

(65) Prior Publication Data

US 2002/0197728 A1 Dec. 26, 2002

Related U.S. Application Data

(60) Provisional application No. 60/170,972, filed on Dec. 15, 1999.

(51) Int. Cl.$^7$ .............................................. G01N 21/64
(52) U.S. Cl. .......................... 436/63; 436/64; 436/164; 436/172
(58) Field of Search ........................... 436/63, 64, 164, 436/172; 382/128–131, 133, 134

(56) References Cited

U.S. PATENT DOCUMENTS

| | | | |
|---|---|---|---|
| 3,013,467 A | 12/1961 | Minsky .......................... 88/14 |
| 3,809,072 A | 5/1974 | Ersek et al. .................. 128/23 |
| D242,393 S | 11/1976 | Bauman | |
| D242,396 S | 11/1976 | Bauman | |
| D242,397 S | 11/1976 | Bauman | |
| D242,398 S | 11/1976 | Bauman | |
| 4,017,192 A | 4/1977 | Rosenthal .................. 356/201 |
| 4,071,020 A | 1/1978 | Pugliese | |
| 4,198,571 A | 4/1980 | Sheppard .................... 250/571 |
| 4,254,421 A | 3/1981 | Kreutel, Jr. ................. 343/754 |
| 4,273,110 A | 6/1981 | Groux | |
| 4,349,510 A | * 9/1982 | Kolehmainen et al. ....... 422/66 |
| 4,357,075 A | 11/1982 | Hunter ....................... 350/294 |
| 4,396,579 A | * 8/1983 | Schroeder et al. ............ 422/52 |
| 4,397,557 A | 8/1983 | Herwig et al. .............. 356/342 |
| 4,515,165 A | 5/1985 | Carroll ....................... 128/664 |
| 4,549,229 A | 10/1985 | Nakano et al. | |
| 4,558,462 A | 12/1985 | Horiba et al. ................. 382/42 |
| 4,641,352 A | 2/1987 | Fenster et al. ................. 382/6 |
| 4,646,722 A | 3/1987 | Silverstein et al. | |
| 4,662,360 A | 5/1987 | O'Hara et al. ................. 128/9 |
| 4,733,063 A | 3/1988 | Kimura et al. .............. 250/201 |
| 4,741,326 A | 5/1988 | Sidall et al. .................. 128/4 |
| 4,753,530 A | 6/1988 | Knight et al. ................. 356/73 |
| 4,755,055 A | * 7/1988 | Johnson et al. ............. 356/440 |
| 4,768,513 A | 9/1988 | Suzuki ....................... 128/634 |
| 4,800,571 A | 1/1989 | Konishi | |
| 4,844,617 A | 7/1989 | Kelderman et al. ......... 356/372 |
| 4,845,352 A | 7/1989 | Benschop .................. 250/201 |
| 4,852,955 A | 8/1989 | Doyle et al. ................ 350/1.2 |
| 4,877,033 A | 10/1989 | Seitz, Jr. ................ 128/660.05 |
| 4,878,485 A | 11/1989 | Adair ........................... 128/6 |
| 4,891,829 A | 1/1990 | Deckman et al. ............... 378/4 |
| 4,930,516 A | 6/1990 | Alfano et al. ............... 128/665 |
| 4,945,478 A | 7/1990 | Merickel et al. ....... 364/413.22 |
| 4,965,441 A | 10/1990 | Picard .................... 250/201.3 |
| 4,972,258 A | 11/1990 | Wolf et al. ................... 358/93 |
| 4,974,580 A | 12/1990 | Anapliotis .................... 128/4 |
| 4,979,498 A | 12/1990 | Oneda et al. .................. 128/6 |
| 4,997,242 A | 3/1991 | Amos ....................... 350/6.91 |
| 5,003,979 A | 4/1991 | Merickel et al. ....... 364/413.22 |
| 5,011,243 A | 4/1991 | Doyle et al. ................. 350/1.2 |
| 5,022,757 A | 6/1991 | Modell ....................... 356/318 |
| 5,028,802 A | 7/1991 | Webb et al. ................. 250/571 |
| 5,032,720 A | 7/1991 | White ........................ 250/236 |
| 5,034,613 A | 7/1991 | Denk et al. ............... 250/458.1 |
| 5,036,853 A | 8/1991 | Jeffcoat et al. ............. 128/634 |
| 5,042,494 A | 8/1991 | Alfano ....................... 128/665 |
| 5,054,926 A | 10/1991 | Dabbs et al. ............... 356/345 |
| 5,065,008 A | 11/1991 | Hakamata et al. .......... 250/216 |
| 5,071,246 A | 12/1991 | Blaha et al. ................ 351/221 |
| 5,074,306 A | 12/1991 | Green et al. ................ 128/664 |
| 5,083,220 A | 1/1992 | Hill ........................... 359/234 |
| 5,091,652 A | 2/1992 | Mathies et al. .......... 250/458.1 |
| 5,101,825 A | 4/1992 | Gravenstein et al. | |
| 5,120,953 A | 6/1992 | Harris ...................... 250/227.2 |
| 5,122,653 A | 6/1992 | Ohki .......................... 250/216 |
| 5,132,526 A | 7/1992 | Iwasaki .................... 250/201.3 |
| 5,139,025 A | 8/1992 | Lewis et al. ................ 128/665 |
| 5,154,166 A | 10/1992 | Chikama ....................... 128/4 |
| 5,159,919 A | 11/1992 | Chikama ....................... 128/4 |
| 5,161,053 A | 11/1992 | Dabbs ........................ 359/384 |
| 5,162,641 A | 11/1992 | Fountain .................. 250/201.2 |
| 5,162,941 A | 11/1992 | Favro et al. ................ 359/386 |
| 5,168,157 A | 12/1992 | Kimura ....................... 250/234 |

(Continued)

FOREIGN PATENT DOCUMENTS

| | | |
|---|---|---|
| EP | 0 135 134 | 3/1985 |
| EP | 0 280 418 | 8/1988 |
| EP | 0 335 725 | 10/1989 |

(Continued)

OTHER PUBLICATIONS

European Search Report for Pending European Patent No. 02 01 9837, Jan. 14, 2004, 4 pgs.

(Continued)

*Primary Examiner*—Jeffrey R. Snay
(74) *Attorney, Agent, or Firm*—Testa, Hurwitz & Thibeault, LLP

(57) ABSTRACT

The invention provides methods and systems for monitoring effects of chemical agents on optical signals produced by samples in response to the chemical agents. Preferred methods comprise application of multiple chemical agents that interact to alter an optical signal from the sample. Methods and systems of the invention also comprise monitoring an optical signal from an endogenous chromophore upon application of a chemical agent to a sample. Methods and systems of the invention also comprise the use of triggers, atomizers and image alignment to enhance the results of methods described herein.

9 Claims, 23 Drawing Sheets

U.S. PATENT DOCUMENTS

| | | | |
|---|---|---|---|
| 5,192,980 A | 3/1993 | Dixon et al. ................. 356/326 |
| 5,193,525 A | 3/1993 | Silverstein et al. |
| RE34,214 E | 4/1993 | Carlsson et al. ............... 358/93 |
| 5,199,431 A | 4/1993 | Kittrell et al. |
| 5,201,318 A | 4/1993 | Rava et al. ................. 128/665 |
| 5,201,908 A | 4/1993 | Jones ............................ 128/4 |
| 5,225,671 A | 7/1993 | Fukuyama .................. 250/216 |
| 5,235,457 A | 8/1993 | Lichtman et al. ........... 359/368 |
| 5,237,984 A | 8/1993 | Williams, III et al. .......... 128/4 |
| 5,239,178 A | 8/1993 | Derndinger et al. ........ 250/234 |
| 5,248,876 A | 9/1993 | Kerstens et al. ............ 250/561 |
| 5,253,071 A | 10/1993 | MacKay |
| 5,257,617 A | 11/1993 | Takahashi ...................... 128/4 |
| 5,260,569 A | 11/1993 | Kimura ....................... 250/234 |
| 5,260,578 A | 11/1993 | Bliton et al. .............. 250/461.1 |
| 5,261,410 A | 11/1993 | Alfano et al. ................ 128/664 |
| 5,262,646 A | 11/1993 | Booker et al. ............... 250/341 |
| 5,274,240 A | 12/1993 | Mathies et al. ........... 250/458.1 |
| 5,284,149 A | 2/1994 | Dhadwal et al. ............ 128/665 |
| 5,286,964 A | 2/1994 | Fountain .................. 250/201.2 |
| 5,289,274 A | 2/1994 | Kondo |
| 5,294,799 A | 3/1994 | Aslund et al. ............ 250/458.1 |
| 5,296,700 A | 3/1994 | Kumagai .................... 250/216 |
| 5,303,026 A | 4/1994 | Strobl et al. ................ 356/318 |
| 5,306,902 A | 4/1994 | Goodman ................ 250/201.3 |
| 5,313,567 A | 5/1994 | Civanlar et al. ............. 395/124 |
| 5,319,200 A | 6/1994 | Rosenthal et al. .......... 250/341 |
| 5,321,501 A | 6/1994 | Swanson et al. ............ 356/345 |
| 5,324,979 A | 6/1994 | Rosenthal ............... 250/504 R |
| 5,325,846 A | 7/1994 | Szabo ............................ 128/4 |
| 5,329,352 A | 7/1994 | Jacobsen .................... 356/301 |
| 5,337,734 A | 8/1994 | Saab ............................. 128/4 |
| 5,343,038 A | 8/1994 | Nishiwaki et al. .......... 250/234 |
| 5,345,306 A | 9/1994 | Ichimura et al. ............ 356/346 |
| 5,398,685 A | 3/1995 | Wilk et al. ................ 128/653.1 |
| 5,402,768 A | 4/1995 | Adair ............................ 128/4 |
| 5,406,939 A | 4/1995 | Bala ............................. 128/4 |
| 5,413,092 A | 5/1995 | Williams, III et al. .......... 128/4 |
| 5,413,108 A | 5/1995 | Alfano ........................ 128/665 |
| 5,415,157 A | 5/1995 | Welcome ....................... 128/4 |
| 5,418,797 A | 5/1995 | Bashkansky et al. ........... 372/3 |
| 5,419,311 A | 5/1995 | Yabe et al. ..................... 128/4 |
| 5,421,337 A | 6/1995 | Richards-Kortum et al. ............... 128/665 |
| 5,421,339 A | 6/1995 | Ramanujam et al. |
| 5,424,543 A | 6/1995 | Dombrowski et al. |
| 5,450,857 A | 9/1995 | Garfield et al. |
| 5,451,931 A | 9/1995 | Muller et al. ................ 340/630 |
| 5,458,132 A | 10/1995 | Yabe et al. ..................... 128/4 |
| 5,458,133 A | 10/1995 | Yabe et al. .................. 600/121 |
| 5,469,853 A | 11/1995 | Law et al. |
| 5,477,382 A | 12/1995 | Pernick ...................... 359/559 |
| 5,480,775 A | 1/1996 | Ito et al. ...................... 435/7.2 |
| 5,493,444 A | 2/1996 | Khoury et al. ............. 359/559 |
| 5,496,259 A | 3/1996 | Perkins |
| 5,507,295 A | 4/1996 | Skidmore ................... 600/121 |
| 5,516,010 A | 5/1996 | O'Hara et al. .............. 600/122 |
| 5,519,545 A | 5/1996 | Kawahara |
| 5,529,235 A | 6/1996 | Bolarski et al. .......... 227/175.1 |
| 5,536,236 A | 7/1996 | Yabe et al. .................. 600/125 |
| 5,545,121 A | 8/1996 | Yabe et al. .................. 600/121 |
| 5,551,945 A | 9/1996 | Yabe et al. .................. 600/122 |
| 5,556,367 A | 9/1996 | Yabe et al. .................. 600/124 |
| 5,587,832 A | 12/1996 | Krause ....................... 359/385 |
| 5,596,992 A | 1/1997 | Haaland et al. ............. 128/664 |
| 5,609,560 A | 3/1997 | Ichikawa et al. ........... 600/101 |
| 5,623,932 A | 4/1997 | Ramanujam et al. ....... 128/665 |
| 5,643,175 A | 7/1997 | Adair ......................... 600/133 |
| 5,647,368 A | 7/1997 | Zeng et al. |
| 5,662,588 A | 9/1997 | Lida ............................ 600/121 |
| 5,685,822 A | 11/1997 | Harhen ....................... 600/125 |
| 5,693,043 A | 12/1997 | Kittrell et al. ................. 606/15 |
| 5,695,448 A | 12/1997 | Kimura et al. .............. 600/121 |
| 5,697,373 A | 12/1997 | Richards-Kortum et al. |
| 5,704,892 A | 1/1998 | Adair ......................... 600/121 |
| 5,707,343 A | 1/1998 | O'Hara et al. .............. 600/121 |
| 5,713,364 A | 2/1998 | DeBaryshe et al. ......... 128/664 |
| 5,730,701 A | 3/1998 | Furukawa et al. .......... 600/127 |
| 5,733,244 A | 3/1998 | Yasui et al. ................. 600/127 |
| 5,735,276 A | 4/1998 | Lemelson |
| 5,746,695 A | 5/1998 | Yasui et al. ................. 600/127 |
| 5,768,333 A | 6/1998 | Abdel-Mottaleb ........... 378/37 |
| 5,769,792 A | 6/1998 | Palcic et al. ................. 600/477 |
| 5,791,346 A | 8/1998 | Craine et al. |
| 5,795,632 A | 8/1998 | Buchalter ................... 428/35.2 |
| 5,800,350 A | 9/1998 | Coppleson et al. .......... 600/372 |
| 5,807,248 A | 9/1998 | Mills .......................... 600/322 |
| 5,813,987 A | 9/1998 | Modell et al. .............. 600/473 |
| 5,817,015 A | 10/1998 | Adair ......................... 600/121 |
| 5,830,146 A | 11/1998 | Skladnev et al. |
| 5,833,617 A | 11/1998 | Hayashi ..................... 600/476 |
| 5,855,551 A | 1/1999 | Sklandnev et al. .......... 600/372 |
| 5,860,913 A | 1/1999 | Yamaya et al. ............. 600/127 |
| 5,863,287 A | 1/1999 | Segawa |
| 5,865,726 A | 2/1999 | Katsurada et al. .......... 600/127 |
| 5,876,329 A | 3/1999 | Harhen ....................... 600/125 |
| 5,920,399 A | 7/1999 | Sandison et al. |
| 5,921,926 A | 7/1999 | Rolland et al. |
| 5,941,834 A | 8/1999 | Skladnev et al. |
| 5,983,125 A | 11/1999 | Alfano et al. |
| 5,989,184 A | 11/1999 | Blair |
| 6,021,344 A | 2/2000 | Lui et al. |
| 6,069,689 A | 5/2000 | Zeng et al. |
| 6,083,487 A | 7/2000 | Biel et al. .................... 424/9.6 |
| 6,096,065 A | 8/2000 | Crowley |
| 6,099,464 A | 8/2000 | Shimizu et al. |
| 6,104,945 A | 8/2000 | Modell et al. .............. 600/473 |
| 6,119,031 A | 9/2000 | Crowley ..................... 600/407 |
| 6,124,597 A | 9/2000 | Shehada et al. |
| 6,146,897 A | 11/2000 | Cohenford et al. ........... 436/63 |
| 6,169,817 B1 | 1/2001 | Parker et al. ............... 382/131 |
| 6,187,289 B1 | 2/2001 | Richards-Kortum et al. . 424/9.8 |
| 6,241,662 B1 | 6/2001 | Richards-Kortum et al. |
| 6,243,601 B1 | 6/2001 | Wist |
| 6,285,639 B1 | 9/2001 | Maenza et al. |
| D453,832 S | 2/2002 | Morrell et al. |
| D453,962 S | 2/2002 | Morrell et al. |
| D453,963 S | 2/2002 | Morrell et al. |
| D453,964 S | 2/2002 | Morrell et al. |
| 6,377,842 B1 | 4/2002 | Pogue et al. |
| D460,821 S | 7/2002 | Morrell et al. |
| 6,571,118 B1 | 5/2003 | Utzinger et al. |
| 6,574,502 B2 | 6/2003 | Hayashi |

FOREIGN PATENT DOCUMENTS

| | | |
|---|---|---|
| EP | 0 474 264 | 3/1992 |
| EP | 0 641 542 | 3/1995 |
| EP | 0 689 045 A1 | 12/1995 |
| EP | 1 104 658 | 6/2001 |
| SU | 1 223 092 | 4/1986 |
| WO | WO 92/19148 | 11/1992 |
| WO | WO 93/14688 | 8/1993 |
| WO | WO 94/26168 | 11/1994 |
| WO | WO 95/04385 | 2/1995 |
| WO | WO 97/05473 | 2/1997 |
| WO | WO 98/30889 | 2/1997 |
| WO | WO 98/24369 | 6/1998 |
| WO | WO 98/41176 | 9/1998 |
| WO | WO 99/18847 | 4/1999 |
| WO | WO 00/57361 | 9/2000 |
| WO | 00/59366 | 10/2000 |

OTHER PUBLICATIONS

Noble et al., "Automated, Nonrigid Alignment of Clinical Myocardial Contrast Echocardiography Image Sequences: Comparison with Manual Alignment," *Ultrasound in Medicine and Biology*, vol 28, No. 1 (2002), pp. 115–123.

Ko et al., "Multiresolution Registration of Coronary Artery Image Sequences," *Internal Journal of Medical Informatics*, vol. 44 (1997), pp. 93–104.

Dickman et al., "Identification of Cervical Neoplasia Using a Simulation of Human Vision" Journal of Lower Genital Tract Disease, vol. 5, No. 3 (2001) pp. 144–152.

Ji et al., "Texture Analysis for Classification of Cervix Lesions" IEEE Transactions on Medical Imaging, vol. 19, No. 11 (Nov. 2000) pp. 1144–1149.

Pogue et al., "Analysis of Acetic Acid–Induced Whitening of High–Grade Squamous Intraepithelial Lesions" Journal of Biomedical Optics, vol. 6, No. 4 (Oct. 2001) pp. 397–403.

Sakuma, T. (1985), "Quantitative Analysis of the Whiteness of the Atypical Cervical Transformation Zone", *The Journal of Reproductive Medicine*, 30(10):773–776.

Tadrous, "Methods for Imaging the Structure and Function of Living Tissues and Cells: 2. Fluorescence Lifetime Imaging," Journal of Pathology, vol. 9, pp. 229–234 (2000).

Balas et al., "In Vivo Detection and Staging of Epithelial Dysplasias and Malignancies Based on the Quantitative Assessment of Acetic Acid—Tissue Interaction Kinetics," Journal of Photochemistry and Photobiology B: Biology, vol. 53, pp. 153–157 (1999).

Balas et al., "In Vivo Assessment of Acetic Acid—Cervical Tissue Interaction Using Quantitative Imaging of BackScattered Light: Its Potential Use for the In Vivo Cervical Cancer Detection Grading and Mapping," Part of the EUROPTO Conference on Optical Biopsy, Stockholm, Sweden, SPIE, vol. 3568 (Sep. 1998).

Balas, "An Imaging Colorimeter for Noncontact Tissue Color Mapping," IEEE Transactions on Biomedical Engineering, vol. 44, No. 6, pp. 468–474 (Jun. 1997).

P. Davidovits et al. "Scanning Laser Microscope for Biological Investigations", Applied Optics, vol. 10, No. 7, pp. 1615–1619, Jul. 1971.

C.J.R. Sheppard et al. "Depth of Field in the Scanning Microscope", Optics Letters, vol. 3, No. 3, Sep. 1978, pp. 115–117.

C.J. Koester, "Scanning Mirror Microscope with Optical Sectioning Characteristics: Applications in Ophthalmology", Applied Optics. vol. 19, No. 11, Jun. 1980, pp. 1749–1757.

T. Wilson., "The Role of the Pinhold in Confocal Imaging Systems", Confocal Microscopy Handbook, pp. 99–113.

C. Koester, "Comparison of Optical Sectioning Methods: The Scanning Slit Confocal Microscope", Confocal Microscope Handbook, pp. 189–194.

Jeffrey W. Hall, et al. "Near–Infrared Spectrophotometry: A New Dimension in Clinical Chemistry", Clin. Chem 38/9, 1623–1631 (1992).

Kevin T. Schomacker, et al. "Ultraviolet Laser–Induced Fluorescence of Colonic Tissue; Basic Biology and Diagnostic Potential", Lasers in Surgery and Medicine, 12: 63–78, (1992).

S. Schwartz, "Real–time laser–scanning Confocal ratio imaging", American Laboratory, pp. 53–62 Apr. 1993.

R. Richards–Kortum et al. Description and Performance of a Fiber–optic Confocal Fluorescence Spectrometer, Applied Spectroscopy, vol. 48, No. 3 pp. 350–355. (1994).

J.M. Schmitt et al. "Interferometric Versus Confocal Techniques for Imaging Microsctructres in Turbid Biological Media", Proc. SPIE, 2135 (1994), pp. 1–12.

N. Ramanujam et al. Fluorescence Spectroscopy; A Diagnostic Tool for Cervical Intraepithelial Neoplasia (CIN), Gynecologic Oncology 52, pp. 31–38 (1994).

S.G. Anderson, "Confocal Laser Microscopes See A Wider Field of Application", Laser Focus World, pp. 83–86, Feb. 1994.

J.M. Schmitt et al. "Confocal Microscopy in Turbid Media", J. Opt. Soc. Am., vol. 11, pp. 2225–2235, Aug. 1994.

N. Ramanujam et al. "In vivo diagnosis of cervical intraepithelial neoplasia using 337–nm–exited laser–induced fluorescence", Pro. Natl. Acad. Sci. USA, vol. 91, pp. 10193–10197, Oct. 1994.

* cited by examiner

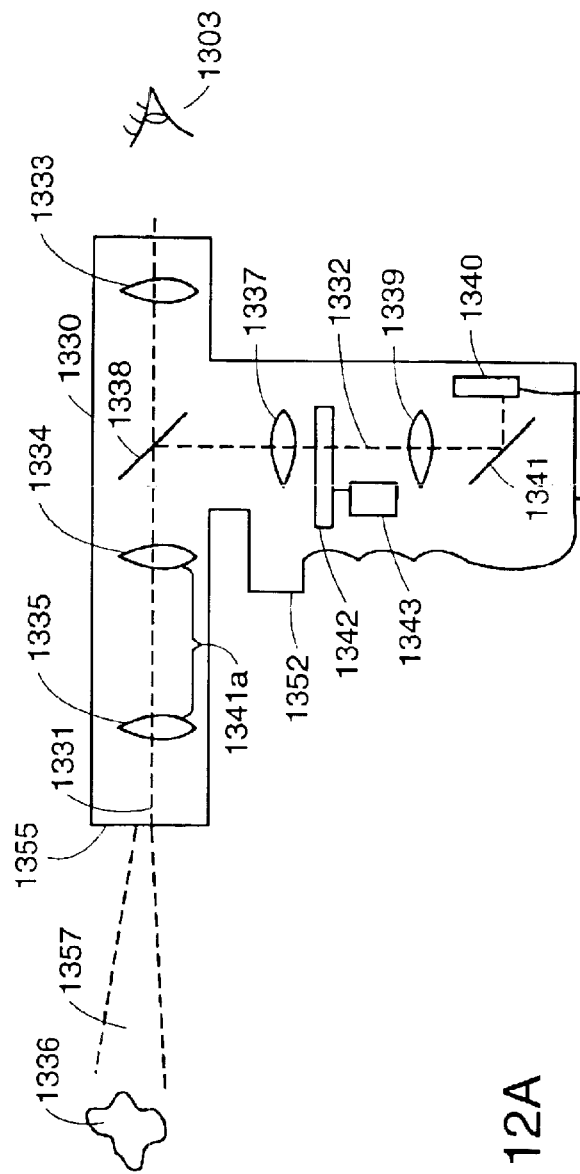
FIG. 11
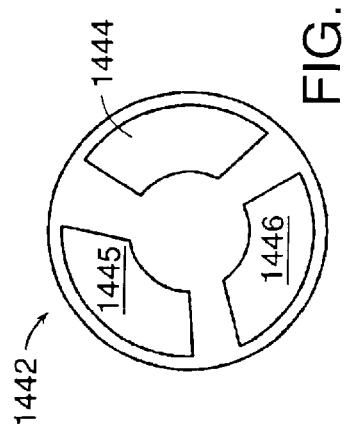
FIG. 12A
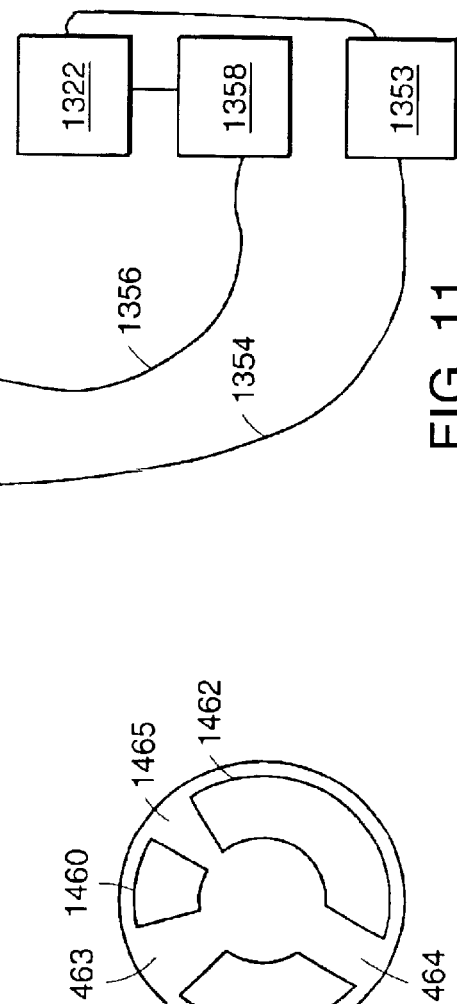
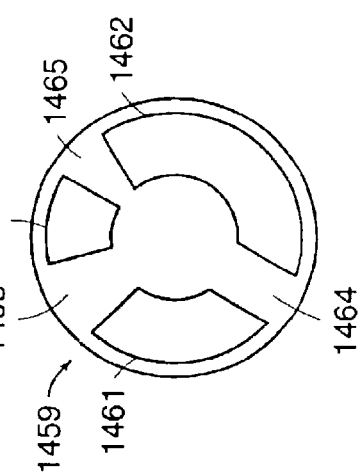
FIG. 12B
FIG. 12C

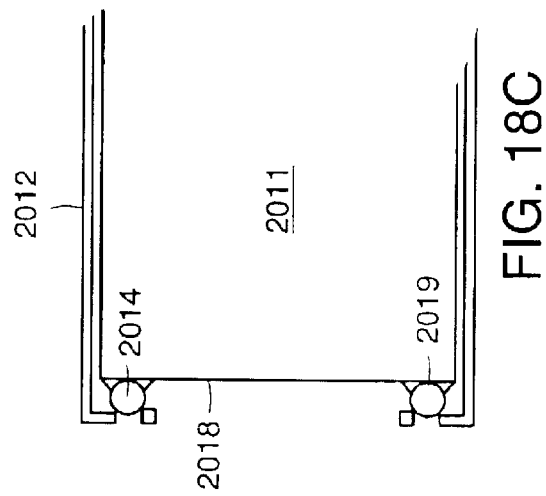
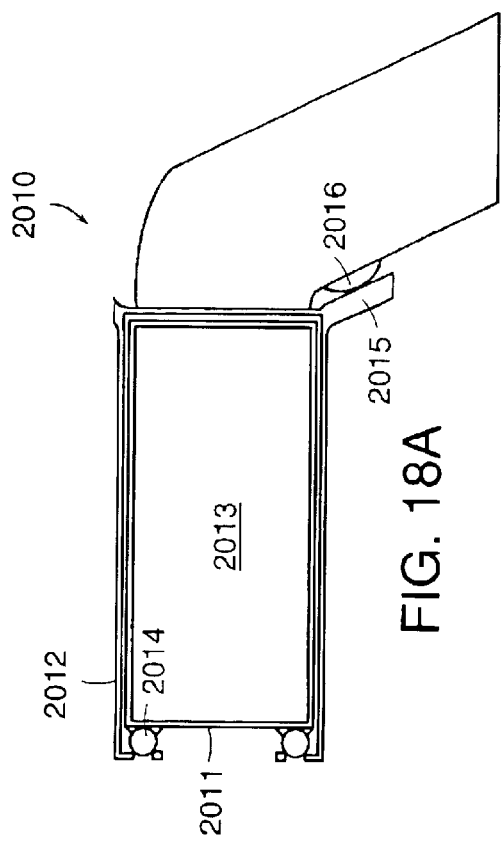
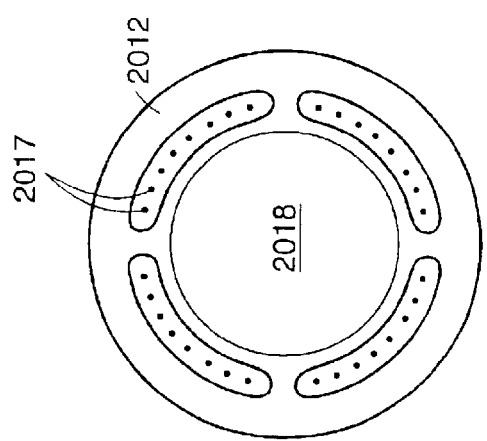
FIG. 18C
FIG. 18A
FIG. 18B

METHODS OF MONITORING EFFECTS OF CHEMICAL AGENTS ON A SAMPLE

CROSS REFERENCE TO RELATED APPLICATIONS

This application claims priority to and the benefit of U.S. provisional patent application Ser. No. 60/170,972, filed Dec. 15, 1999, the disclosure of which application is hereby incorporated by reference.

FIELD OF THE INVENTION

This invention relates generally to spectral analysis. More particularly, in one embodiment, the invention relates to determining chemically-induced changes of optical spectra.

BACKGROUND OF THE INVENTION

Direct visual observation alone is often inadequate for identification of abnormalities in a specimen being examined, whether the specimen is a biological specimen or otherwise. Observation of many medical conditions in biological specimens of all kinds is well known. It is common in medical examination to perform visual examinations in disease diagnosis. For example, visual examination of the cervix can discern areas where there is a "suspicion" of pathology. In some instances, filters can be used to improve visual differentiation of normal and abnormal tissues. In other situations, when tissues of the cervix are examined in vivo, chemical agents such as acetic acid can be applied to enhance the differences in appearance between normal and pathological areas. These techniques form an integral part of a colposcopic examination of the cervix. Colposcopists may amplify the difference between normal and cancerous tissue with the application of various "activation" agents, the most common being acetic acid, at approximately 3% to 5% concentration, or an iodine solution, such as Lugol's iodine or Shiller's iodine. Even when the cervical tissues are viewed through a colposcope by an experienced practitioner with the application of acetic acid, correct diagnosis can be affected by subjective analysis. A variety of methods using optical techniques have been directed towards the diagnosis of cancer and other pathologies, particularly involving the cervix. Certain of these systems and methods have limitations that render them unsuitable for use as screening procedures.

While there have been extensive developments in the field of cancer diagnosis, none of these are well adapted for screening large populations. Currently, disease diagnoses are made predominately from pathological examinations of biopsied tissue. Techniques such as biopsies, while being the definitive determination of the presence of disease, are labor-intensive and operator-dependent, thus unsuitable for screening large populations. As another example, medical imaging techniques, depending on their cost, resource requirements and patient accessibility, may be unsuitable for population screening.

To be well accepted in the medical community, a screening method should be sufficiently sensitive and specific to identify abnormalities accurately. Furthermore, a screening method ideally is easy to perform so that it can be carried out rapidly on an otherwise healthy patient. In addition, to be cost effective the screening method should not require the use of expensive resources, including a significant time commitment from costly, highly trained medical personnel. Generally, screening settings advantageously employ less skilled operators and more operator-independent technology.

SUMMARY OF THE INVENTION

The invention provides systems and methods for quickly and efficiently screening samples, especially biological samples. According to the invention, changes in the spectral properties of tissues upon exposure to chemical agents are characteristic of the physiological state of the tissue. In particular, the invention relates to changes in spectral properties of a sample in response to chemical treatment. The sample can be a sample of tissue, and the response can be indicative of a state of health of the tissue or the patient from whom the sample is obtained. Upon exposure to chemical agents, the light emission properties of a sample change. In the case of a sample of tissue, the temporal evolution of these changes is characteristic of the state of health of the tissue generally. When exposed to light, tissues emit light having spectral properties that are characteristic of the physiological and biochemical make-up of the tissue. When exposed to a chemical agent, such as a contrast agent, the spectral properties of the tissue are changed by the interaction of the agent with endogenous molecules in the tissue. As the chemical agent diffuses out of the area of application, or otherwise becomes less abundant in the tissue, the emission spectrum of the tissue returns to pre-exposure levels. According to the invention, changes in tissue produced by endogenous chemical agents provide insight into the sample, such as the clinical health of the tissue as described in detail below. The invention also involves systems and methods of performing the application of one or more chemical agents, including the amount of material dispensed, dispensing patterns, and triggering a measurement relative to the time of dispensing.

Accordingly, the invention provides methods and systems for monitoring effects of chemical agents on a sample by exposing a sample to one or more chemical agents, and measuring a change in an optical signal from the sample. A preferred method of the invention comprises dispensing a plurality of chemical agents on a sample, wherein the agents interact to alter an optical signal from the sample and measuring the chemical agents are selected from the group consisting of acetic acid, formic acid, propionic acid, butyric acid, Lugol's iodine, Shiller's iodine, methylene blue, toluidine blue, osmotic agents, ionic agents, and indigo carmine. The chemical agents may be applied substantially simultaneously, or by dispensing at least two of the plurality of chemical agents sequentially.

The invention is applicable to any sample type. Preferred methods of the invention comprise using a biological sample. In a preferred embodiment, the sample is selected from epithelial tissue, cervical tissue, colorectal tissue, skin, and uterine tissue.

In another aspect, a preferred embodiment of the invention relates to a method of monitoring effects of a chemical agent on a sample comprising dispensing a chemical agent on a sample, providing an automated triggering signal to initiate a measurement period relative to the dispensing, and measuring an optical signal from the sample. The automated triggering signal can be provided prior to, substantially simultaneously with, or after dispensing the chemical agent. In preferred embodiments, the measurement is initiated at a predetermined time relative to the automatic triggering signal. In yet another aspect, methods of the invention comprise of diagnosing the state of health of a applying the chemical agent or agents as a mist onto the sample.

In a preferred embodiment, the predefined pattern is substantially circular. In another preferred embodiment, the predefined pattern is substantially annular.

In preferred embodiments, the chemical agent is dispensed at a controlled rate, or a controlled volume of the chemical agent is dispensed, or both.

In a still further aspect, the invention comprises dispensing a chemical agent on a sample, capturing a plurality of sequential images of the sample during a measurement period, automatically aligning a subset of the plurality of images to spatially correlate the subset of images, measuring an optical signal from the subset of the spatially correlated images, and providing a diagnosis of a state of health of the sample based at least in part on the optical signal.

In a preferred embodiment, aligning further comprises aligning the subset to compensate for relative motion between the sample and a spectral observation device. In another preferred embodiment, aligning further comprises aligning the subset to compensate for relative motion between a first portion of the sample and a second portion of the sample.

In a still further aspect, the invention provides methods for determining a tissue response in which a chemical agent is applied to a tissue and an optical property of an endogenous molecule in the tissue is measured. In a preferred embodiment. the endogenous molecule is a chromophore, for example a fluorophore. Method of the invention comprise applying the chemical agent and monitoring an optical signal from the endogenous molecule. The presence, absence, or change in the signal may be indicative of disease when compared to known standards. Such standards may be empirically derived or may be obtained from the art. The endogenous chromophore is preferably hemoglobin, a porphoryin, NADH, a flavin, elastin, or collagen.

In preferred methods, the optical signal is a light signal, such as a fluorescent or white light spectrum. The optical signal may also be a spectrum produced, at least in part by light-scattering properties of the tissue.

Also in preferred methods, the optical signal may be a decay function. The optical signal is compared to a standard response associated with healthy or diseased tissue, including tissue at various stages of disease. Such standards may be determined empirically or known in the art. Alteration of an optical signa alone may be indicative of the health of the patient from whom a sample was obtained.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 11 is a functional block diagram of an embodiment of an illustrative hand-held system useful for monitoring the effects of a chemical agent on a specimen according to the invention;

FIGS. 12A–12C depict schematic arrangements for illustrative filter wheels useful in the system of FIG. 11;

FIGS. 18A–18C are diagrams depicting various aspects of a mucosal atomizer device used to spray a chemical agent uniformly onto the surface of a specimen, and to provide a trigger mechanism useful for initiating an optical observation, according to principles of the invention;

DETAILED DESCRIPTION

Acetowhitening of cervical tissue has long been known to be a qualitative aid to locating lesions during colposcopic examination. However, accurate quantitative measurements of acetowhitening of cervical epithelial tissue, as a function of time and wavelength, have not been reported. Quantitative analysis of the acetowhitening process can significantly increase the sensitivity and specificity of traditional colposcopy.

The invention will be described in terms of multiple embodiments that relate to the observation of chemically-induced changes in optical spectra, particularly in the area of medical diagnostics, and especially as it relates to the analysis of spectra obtained from human cervical tissue in the detection of cervical cancer. However, the invention has applicability generally in the area of chemically-induced changes in optical spectra.

Figure 1:
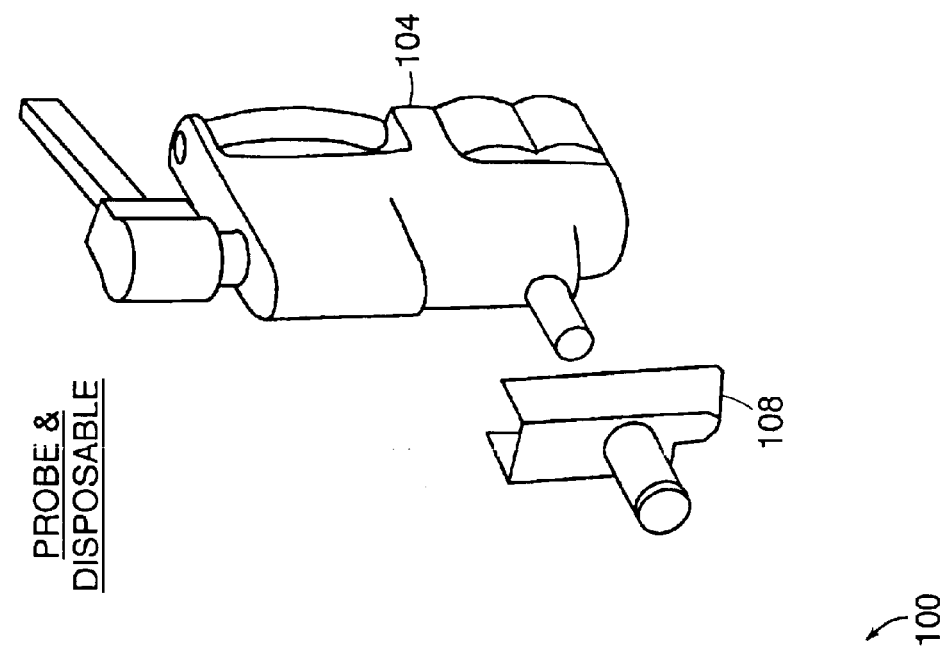
FIG. 1 shows an exemplary spectroscopic system that employs a plurality of spectral types according to an illustrative embodiment of the invention.
Figure 1:
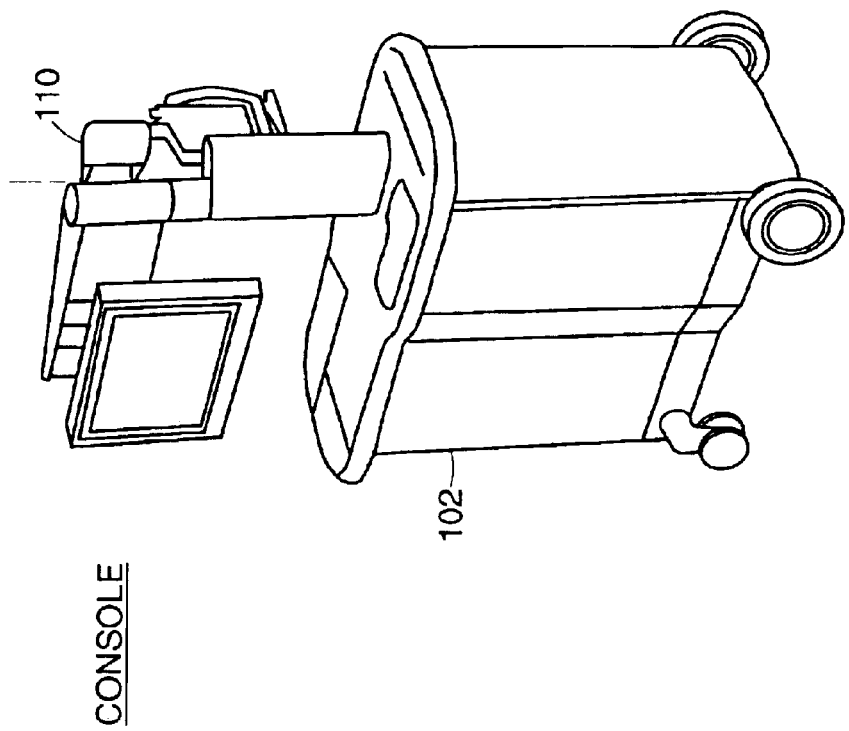

FIG. 1 depicts an exemplary spectroscopic system 100 employing a plurality of spectral data types in methods and systems according to an illustrative embodiment of the invention. The spectroscopic system includes a console 102 connected to a probe 104 by a cable 106. The cable 106 carries electrical and optical signals between the console 102 and the probe 104. The probe 104 accommodates a disposable component 108 which is used only once, and discarded after use. The console 102 and the probe 104 are mechanically connected by an articulating arm 110, which can also support the cable 106. The console 102 contains much of the hardware and the software of the system, and the probe 104 contains the necessary hardware for making suitable spectroscopic observations. The details of the system are further explained in conjunction with FIG. 2.

Figure 2:
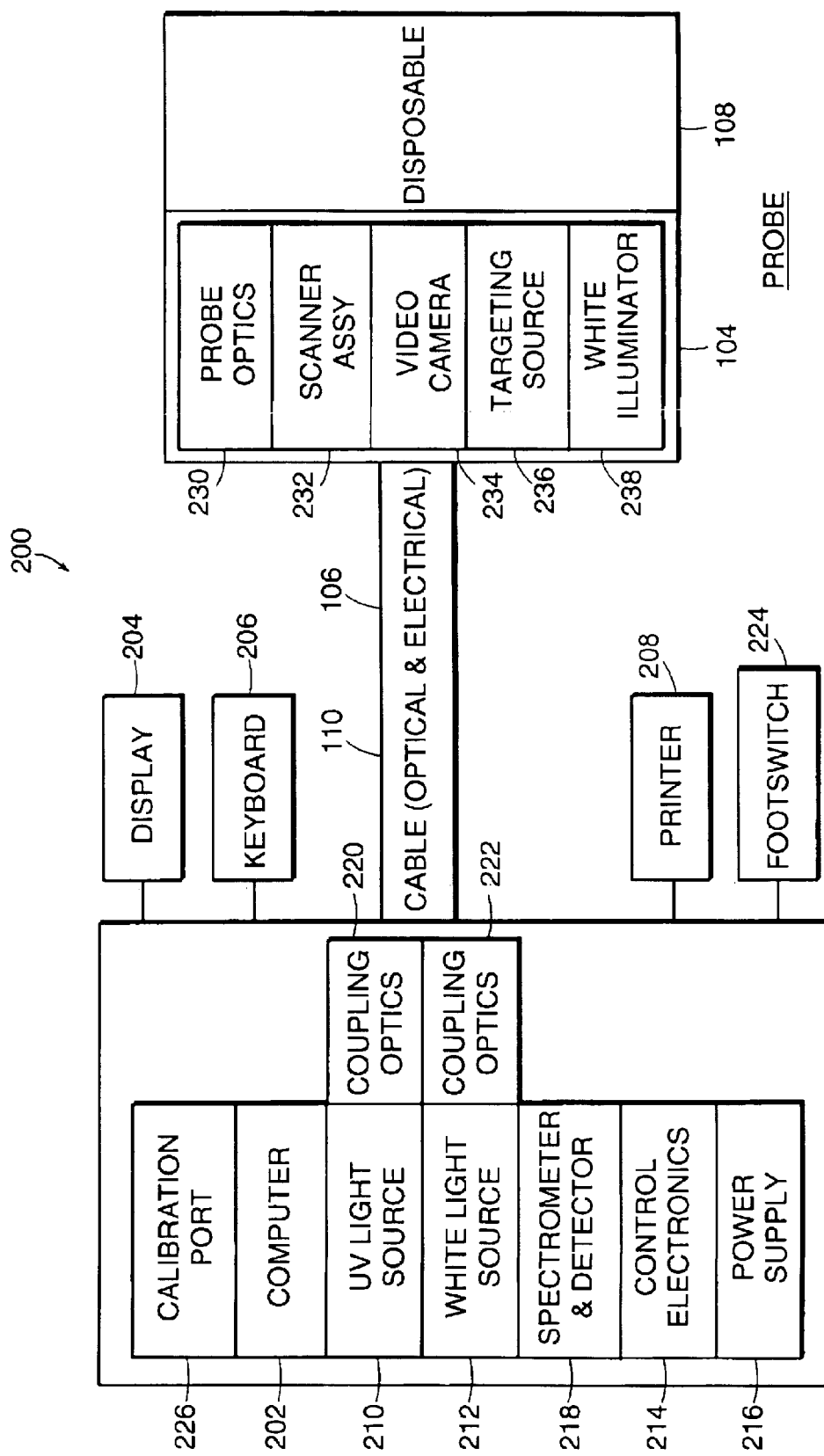
FIG. 2 shows an exemplary operational block diagram of the spectroscopic system of FIG. 1.

FIG. 2 shows an exemplary operational block diagram 200 of a spectroscopic system of the type depicted in FIG. 1. According to an illustrative embodiment, the spectroscopic system of FIGS. 1 and 2 is subtantially the same as single-beam spectrometer devices, but is adapted to include the features of the invention. The console 102 includes a computer 202 which executes software that controls the operation of the spectroscopic system 100. The software includes one or more modules recorded on machine-readable media, which can be any medium such as magnetic disks, magnetic tape, CD-ROM, semiconductor memory, or the like. Preferably, the machine-readable medium is resident within the computer 202. In alternative embodiments, the machine-readable medium can be connected to the computer 202 by a communication link. In alternative embodiments, one can substitute computer insructions in the form of hardwired logic for software, or one can substitute firmware (i.e., computer instructions recorded on devices such as PROMs, EPROMS or EEPROMs, or the like) for software. The term machine-readable instructions as used herein is intended to encompass software, hardwired logic, firmware and the like.

The computer 202 is a general purpose computer. The computer 202 can be an embedded computer, or a personal computer such as a laptop or desktop computer, that is capable of running the software, issuing suitable control commands, and recording information in real time.

The computer 202 has a display 204 for reporting information to an operator of the spectroscopic system 100, a keyboard 206 for enabling the operator to enter information and commands, and a printer 208 for providing a print-out, or permanent record, of measurements made by the spectroscopic system 100 and for printing diagnostic results, for example, for inclusion in the chart of a patient. As described below in more detail, in an illustrative embodiment of the invention, some commands entered at the keyboard, enable a user to select a particular spectrum for analysis or to reject a spectrum, and to select particular segments of a spectrum for normalization. Other commands enable a user to select the wavelength range for each particular segment and to specify both wavelength contiguous and non-contiguous segments.

The console 102 also includes an ultraviolet (UV) source 210 such as a nitrogen laser or a frequency-tripled Nd:YAG laser, a white light source 212 such as one or more Xenon flash lamps, and control electronics 214 for controlling the light sources both as to intensity and as to the time of onset of operation and the duration of operation. One or more power supplies 216 are included in the console 102, to provide regulated power for the operation of all of the components. The console 102 also includes at least one spectrometer and at least one detector (spectrometer and detector 218) suitable for use with each of the light sources. In some embodiments, a single spectrometer can operate with both the UV light source and the white light source. In some embodiments, the same detector can record UV and white light signals, and in some embodiments different detectors are used for each light source.

The console 102 also includes coupling optics 220 to couple the UV illumination from the UV light source 210 to one or more optical fibers in the cable 106 for transmission to the probe 104, and for coupling the white light illumination from the white light source 212 to one or more optical fibers in the cable 106 for transmission to the probe 104. The console 102 also includes coupling optics 222 to couple the spectral response of a specimen to UV illumination from the UV light source 210 observed by the probe 104 and carried by one or more optical fibers in the cable 106 for transmission to the spectrometer and detector 218, and for coupling the spectral response of a specimen to the white light illumination from the white light source 212 observed by the probe 104 and carried by one or more optical fibers in the cable 106 for transmission to the spectrometer and detector 218. The console 102 includes a footswitch 224 to enable an operator of the spectroscopic system 100 to signal when it is appropriate to commence a spectral observation by stepping on the switch. In this manner, the operator has his or her hands free to perform other tasks, for example, aligning the probe 104.

The console 102 includes a calibration port 226 for calibrating the optical components of the spectrometer system. The operator places the probe 104 in registry with the calibration port 226 and issues a command that starts the calibration operation. In the calibration operation, a calibrated light source provides illumination of known intensity as a function of wavelength as a calibration signal. The probe 104 detects the calibration signal. The probe 104 transmits the detected signal through the optical fiber in the cable 106, through the coupling optics 222 to the spectrometer and detector 218. A test spectral result is obtained. A calibration of the spectral system is computed as the ratio of the amplitude of the known illumination at a particular wavelength divided by the test spectral result at the same wavelength.

The probe 104 includes probe optics 230 for illuminating a specimen to be analyzed with UV and white light from the UV source 210 and the white light source 212, and for collecting the fluorescent and backscatter (or reflectance) illumination from the specimen that is being analyzed. The probe includes a scanner assembly 232 that provides illumination from the UV source 210 in a raster pattern over a target area of the specimen of cervical tissue to be analyzed. The probe includes a video camera 234 for observing and recording visual images of the specimen under analysis. The probe 104 includes a targeting souce 236, which can be used to determine where on the surface of the specimen to be analyzed the probe 104 is pointing. The probe 104 also includes a white light illuminator 238 to assist the operator in visualizing the specimen to be analyzed. Once the operator aligns the spectroscopic system and depresses the footswitch 224, the computer 202 controls the actions of the light sources 210, 212, the coupling optics 220, the transmission of light signals and electrical signals through the cable 106, the operation of the probe optics 230 and the scanner assembly 232, the retreival of observed spectra via the cable 106, the coupling of the observed spectra via the coupling optics 222 into the spectrometer and detector 218, the operation of the spectrometer and detector 218, and the subsequent signal processing and analysis of the recorded spectra.

Figure 3:
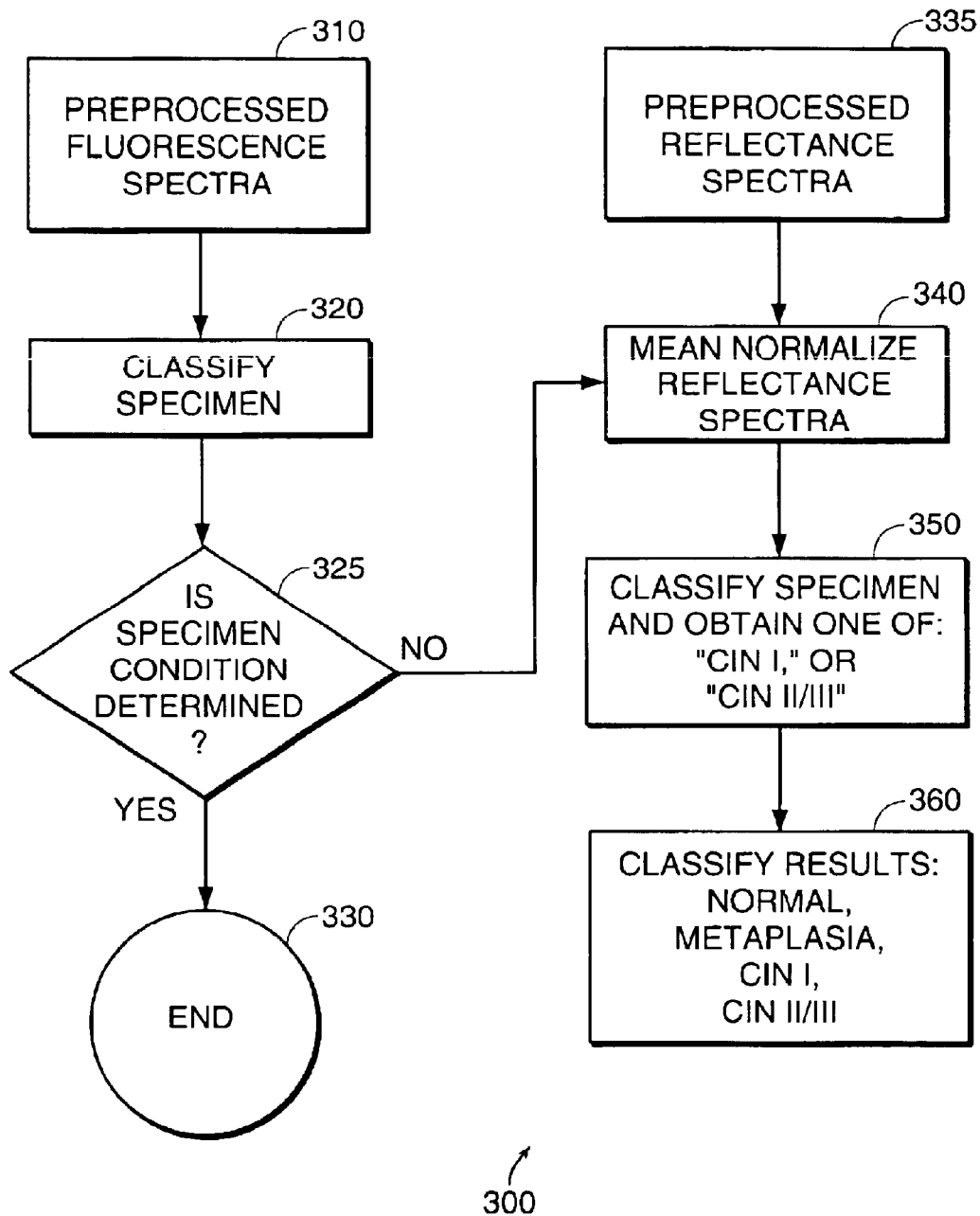
FIG. 3 is a detailed schematic flow diagram showing exemplary steps of combining a fluorescence spectrum analysis with a reflectance spectrum analysis according to an illustrative embodiment of the invention.

FIG. 3 is a detailed schematic flow diagram 300 showing exemplary steps of combining fluorescence spectrum analysis with reflectance spectrum analysis to perform tissue characterization according to an illustrative embodiment of the invention. Step 310 indicates that fluorescence spectra from a test specimen of unknown condition or unknown state of health are available. At step 320, the computer 202 determines whether the test specimen can be classified as "normal," or "metaplasia," or can not be classified by fluorescence spectroscopy alone. As indicated in step 325, a decision is taken as to whether the test specimen has a definitive state of health, for example that the specimen is "normal." If the test specimen can be classified, for example as normal, the method ends at step 330.

In the event that a definitive condition or state of health cannot be ascribed to a test specimen, the computer 202 further analyses information available from a reflectance spectrum or from a plurality of reflectance spectra taken from the test specimen. At step 335, the computer 202 provides processed reflectance spectra.

If the specimen cannot be classified, a mean normalization step is performed by computer 202, as indicated at step 340. The mean normalization is carried out using a plurality of reflectance spectra taken from specimens that are known to represent normal squamous tissue. In one embodiment, a single test specimen is examined at multiple locations, each location measuring approximately one millimeter in diameter. If one or more locations of the test specimen provide fluorescence spectra that indicate that those locations can be classified as representing normal squamous tissue, the reflectance spectra recorded from those locations are used to mean normalize the reflectance spectra obtained from locations that are not capable of being classified as "normal" or "metaplasia" solely on the basis of fluorescence spectra.

As indicated in step 350, the computer 202 can carry out an analysis using a metric, for example using the Mahalanobis distance as a metric in N-dimensional space. In one embodiment, the test reflectance spectra are truncated to the wavelength regions 391 nm to 484 nm, and 532 nm to 625 nm. In one embodiment, the classifications CIN I and CIN II/II are the classifications that are possible for a test spectrum that is neither classified as "normal" nor "metaplasia" by fluorescence spectral analysis. As indicated at step 350, the computer 202 classifies the test specimen as having a condition or state of health selected from CIN I and CIN II/III based on the value of the metric computed by the computer 202, provided that the value of the metric does not exceed a pre-determined maximum value.

At step 360, the computer 202 presents the results of the classification of the test specimen, as a condition or state of health corresponding to one of normal, metaplasia, CIN I and CIN II/III.

Figure 4:
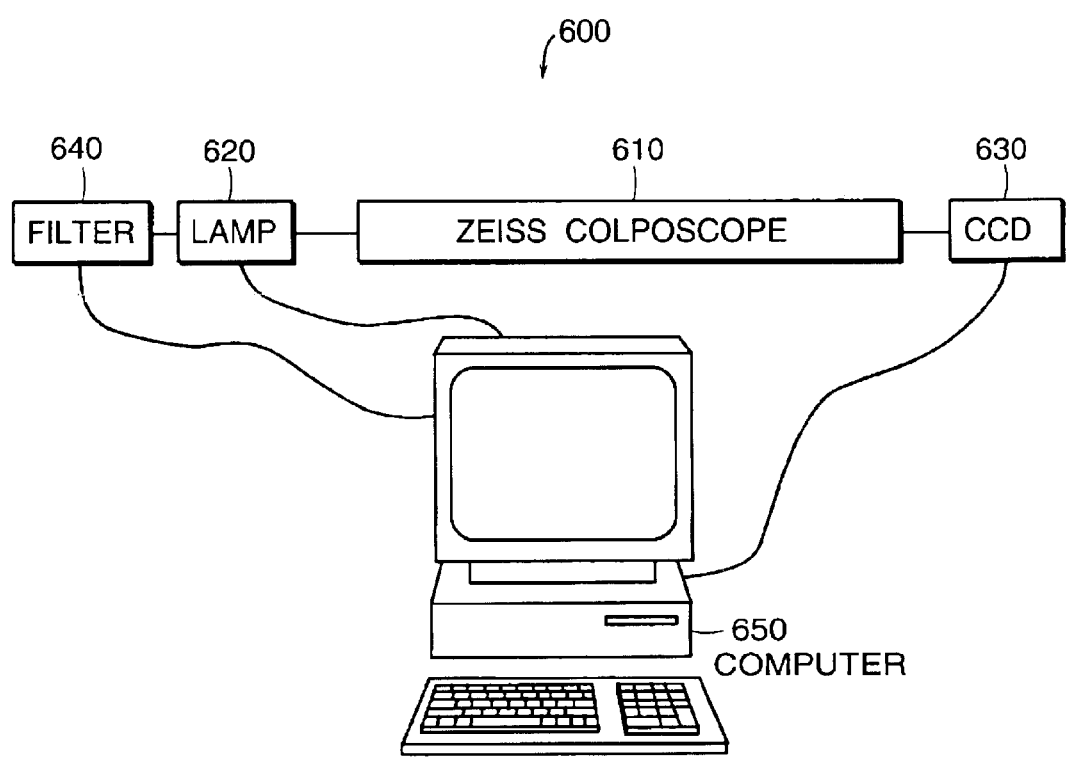
FIG. 4 is a schematic diagram of another illustrative system useful for monitoring the effects of a chemical agent on a specimen, and which embodies principles of the invention.

FIG. 4 shows a schematic diagram of an illustrative system 600 embodying principles of the invention. A standard colposcope 610 (Zeiss, Model 1-FC ZMS-506-II) is modified by adding video image capture capability with permanent and electronic storage of data to allow capturing of time-sequenced images during a routine colposcopic examination. The colposcope 610 has magnification capabilities of 4×, 6×, 10×, 16×, and 25×, and is illuminated by a fiber optic-coupled 12 volt/100 watt halogen lamp 620 with 20× eye binoculars. A three-channel charge-coupled device color video camera (DAGE-MTI, Model DC-330) 630 is mounted to the colposcope 610. The computer 650 includes an integrated video frame-grab board and video display card at 24-bit resolution for capturing images. Images can be captured at a rate of at least about one image per second. The computer 650 also includes image control software (TeleComputing Solutions, ColpoShot™) that interfaces with the video frame grab board for archiving images, for example into patients' medical records. The ColpoShot™ software is modified to allow for intensity measurements at specific sites as a function of time and wavelength (as resolved by four discrete filters in a filter wheel 640, described in more detail below). The computer 650 also includes control software for controlling the change of filters in the high-speed filter wheel 640. This software is synchronized with the data collection (image capture) software so each image is associated with a spectral region corresponding to a particular filter. Time-stamping of each image is performed so each image can be placed in proper time sequence.

In the illustrative system 600, the filter wheel 640 is from a Ludl Electronics Ltd., with an RS 232 and GPIB 488 computer interface for resolving optical signals with respect to wavelength. Images are measured and recorded at three separate wavelength bands in the visible spectral region. The first wavelength band is near 400 nm, with a bandwidth of about 20 nm to about 30 nm. The second wavelength band is near 525 nm with a bandwidth of about 30 nm. The third wavelength band is near 680 nm with a nominal bandwidth of about 30 nm. In addition to the images taken through the filter wheel 640, a fourth image using unfiltered illumination is taken as part of the data set. The unfiltered images allow data analysis of red (R), green (G), and blue (B) components for comparison with filtered image data. As described before, crossed polarizers mounted in the optical path, one associated with the light coming from the illumination source 620, and one associated with the light from the image to be observed and recorded, are used to reduce unwanted glare from the surface of the cervix.

The illustrative system 600 is controlled by the computer 650, having capabilities similar to the computer 140 described earlier. The computer 650 has associated with it software to operate the computer 650, to provide input and output interactions with an instrument user, to control and synchronize the various components of the illustrative system 600, and to record, analyze, and report data obtained from the illustrative system 600.

The illustrative system 600 is configured to capture time-separated images of the specimen during routine colposcopic examinations. Digital images are recorded at a 4× magnification giving a panoramic view of the entire cervical field at maximal acetic whitening. In the illustrative embodiment, images are taken about every second for about 5 minutes after the application of acetic acid. The computer 650 rotates the filter wheel 640 to allow for imaging at different wavelengths.

In operation, an illustrative embodiment of the process of obtaining images is as follows. The first image following the application of the acetic acid is an unfiltered image. Next, the filter wheel 640 is rotated to bring the short-wavelength (~400 nm) filter into place and the next image is recorded. Then, the ~525 nm filter is positioned, and the next image is recorded. Next, the long-wavelength (~680 nm) filter is positioned and the last image of the sequence is recorded. This process takes four seconds to complete. After this first cycle through the filter wheel 640, the process repeats with another unfiltered image, followed by the sequence of filtered images. The process of observing and recording images continues without stopping for a duration of 300 seconds. The resulting data are seventy-five unfiltered images of the evolution of an optical signal from a specimen treated with a chemical agent, such as cervical acetowhitening, and a total of seventy-five images in each of the three filtered spectral regions. As will be appreciated by those of skill in the spectroscopic arts, the precise sequence of observing and recording images in the various wavelength bands depends on the sequence of placement of filters within the filter wheel 640 and the sense of rotation of the wheel 640. Alternative sequences of observation can be employed with substantially equivalent results. The duration of operation can be shortened or extended from the illustrative 300 seconds just described depending on the situation, which can be influenced by the kind of specimen and how it is to be examined (e.g., specimen characteristics, such as cervix, larynx, skin, and the like, specimen in vivo or in vitro, use of different chemical agents, the disease conditions to be investigated, and the like).

Illustratively, time-stamped images are saved to disk at 20 second intervals. In one embodiment, treatment of a specimen with a chemical agent is accomplished as follows. A solution of 5% acetic acid is applied with solution-soaked cotton balls placed in contact with the surface of the cervix for about 15 seconds. An alternative method of application of a chemical agent is discussed below. In one embodiment, the time sequence image capturing software is run immediately before the application of acetic acid, to obtain baseline measurements.

In one embodiment, the parameters that are extracted from the observations include the rate of acetowhitening, the maximum intensity of the whitening, and the final rate of decay of the whitening. Once the data is collected, the images are analyzed by the computer 650 with software that calculates four parameters (mean Luminance, and mean red (R), green (G), and blue (B) intensities) within user-defined Regions of Interest (ROI's). The software enables the user to mark, with a mouse controlled cross-hair cursor, 5 pixel by 5 pixel ROI's on a location in an image. A biopsy can subsequently be taken by the colposcopist, to permit a comparison of the results obtained from the methods of the invention with the results of the biopsy. Once ROI's have been manually marked on all images in the timed-sequence, mean Luminance and mean R, G, B intensities within the 5 pixel by 5 pixel ROI's are calculated and output in tabular form. Also included in the output recorded in the table are the following data elements; image number, ROI location, elapsed time in seconds, and the standard deviation and median of the Luminance and R, G, B values. In one embodiment, the ratio of the mean green intensity to the mean red intensity is found to yield accurate results.

In this embodiment, to calibrate the utility of the system and method, five (5) biopsy-confirmed CIN II/III lesions are measured, five (5) biopsy-confirmed CIN I lesions are measured, five (5) colposcopy-confirmed normal mature squamous tissue regions are measured and one (1) biopsy-confirmed normal mature squamous tissue region is measured. Data are analyzed by graphing the Green intensity divided by the Red intensity and normalizing by the maximum intensity within each patient.

Figure 5:
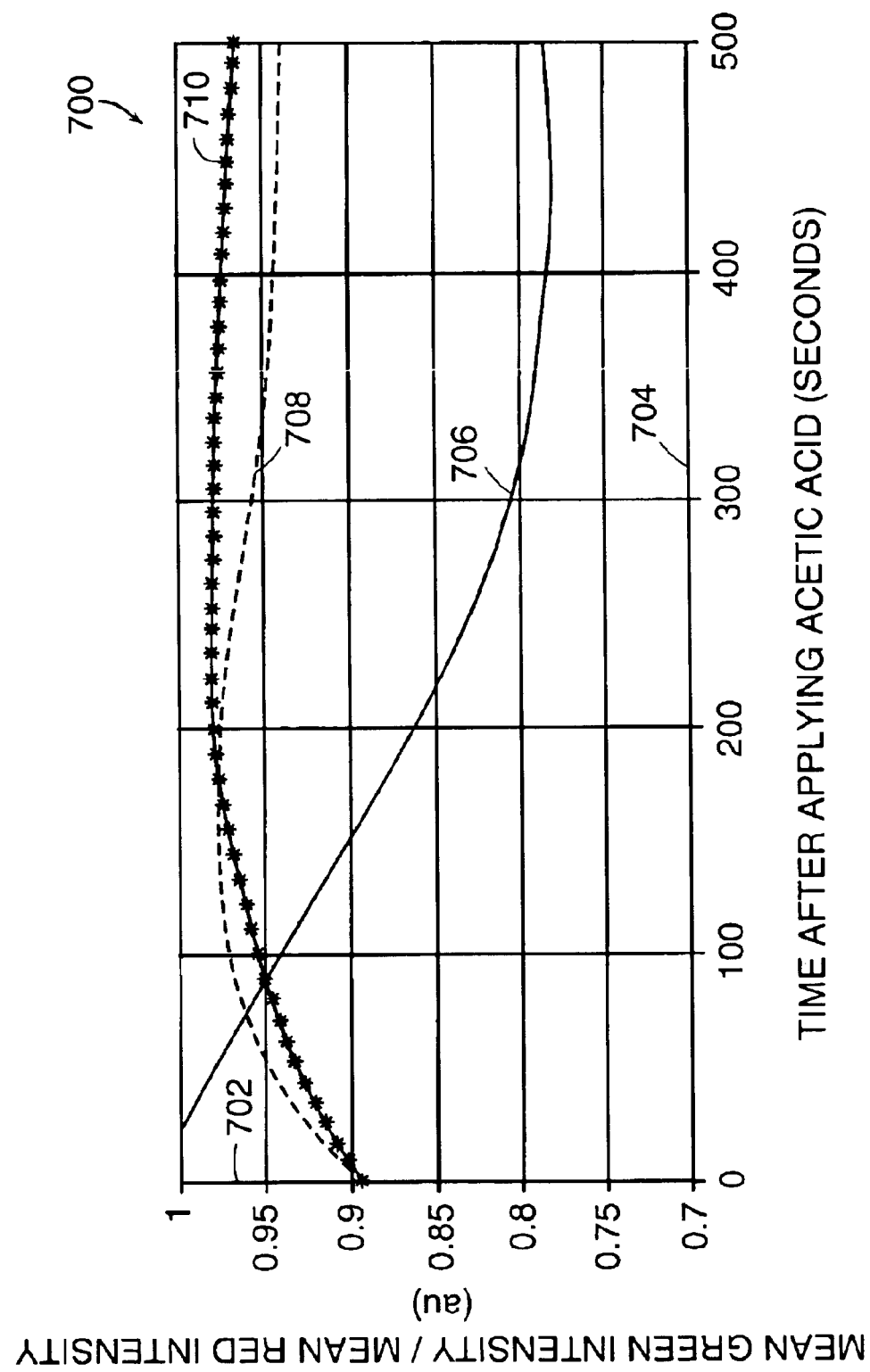
FIG. 5 is a graph that shows trend lines of data observed according to principles of the invention.

FIG. 5 is a diagram 700 that shows the trend lines of ROIs correlated to CIN II/III lesions (curve 706), CIN I lesions (curve 708), and normal mature squamous tissue (curve 710). The trend lines are plotted using the ratio of mean green intensity to mean red intensity, normalized to maximum intensity, as the vertical axis 702 (expressed in arbitrary units), and using the time after application of acetic acid to the tissue, expressed in seconds, as the horizontal axis 704.

Figure 6A:
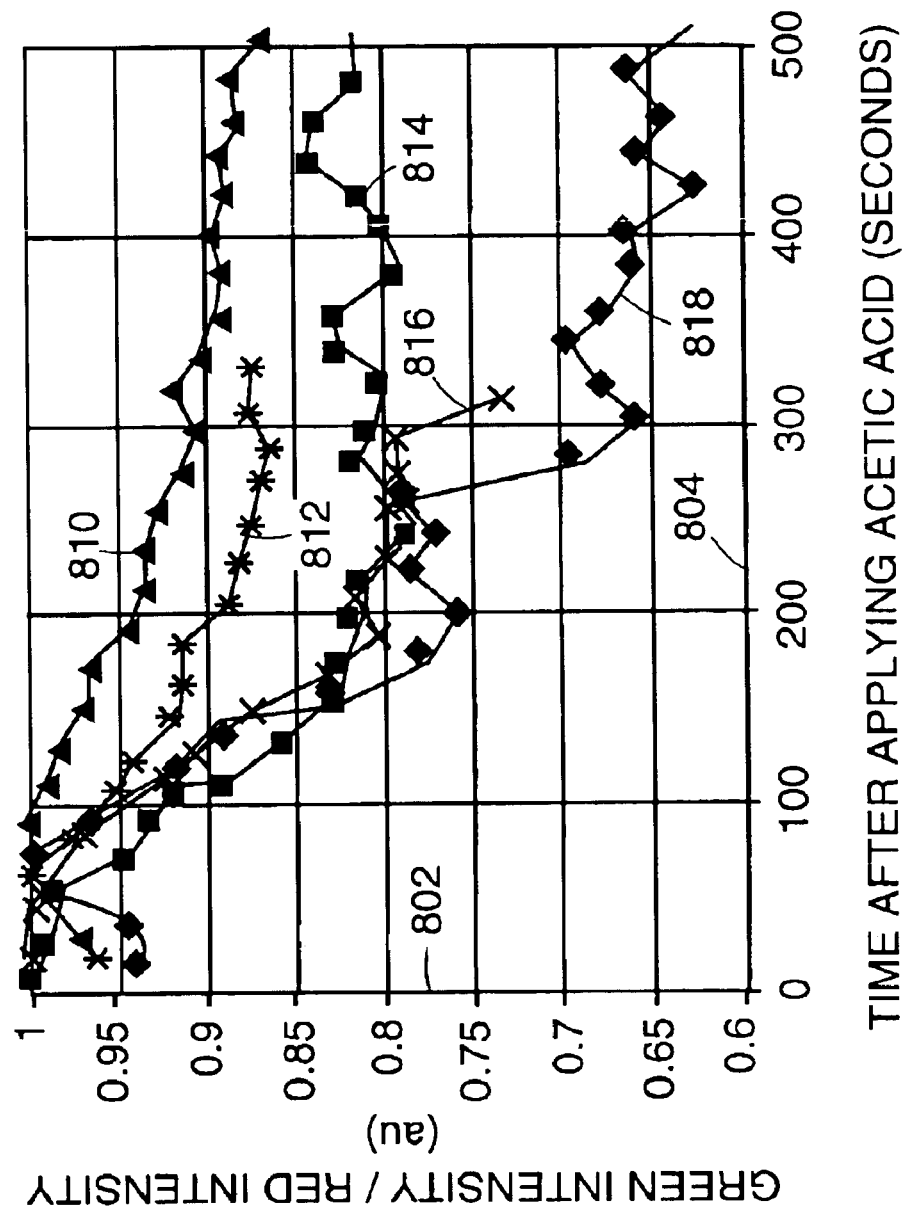
FIGS. 6A–6C are diagrams that show raw data observed from various specimens, according to principles of the invention;.
Figure 6B:
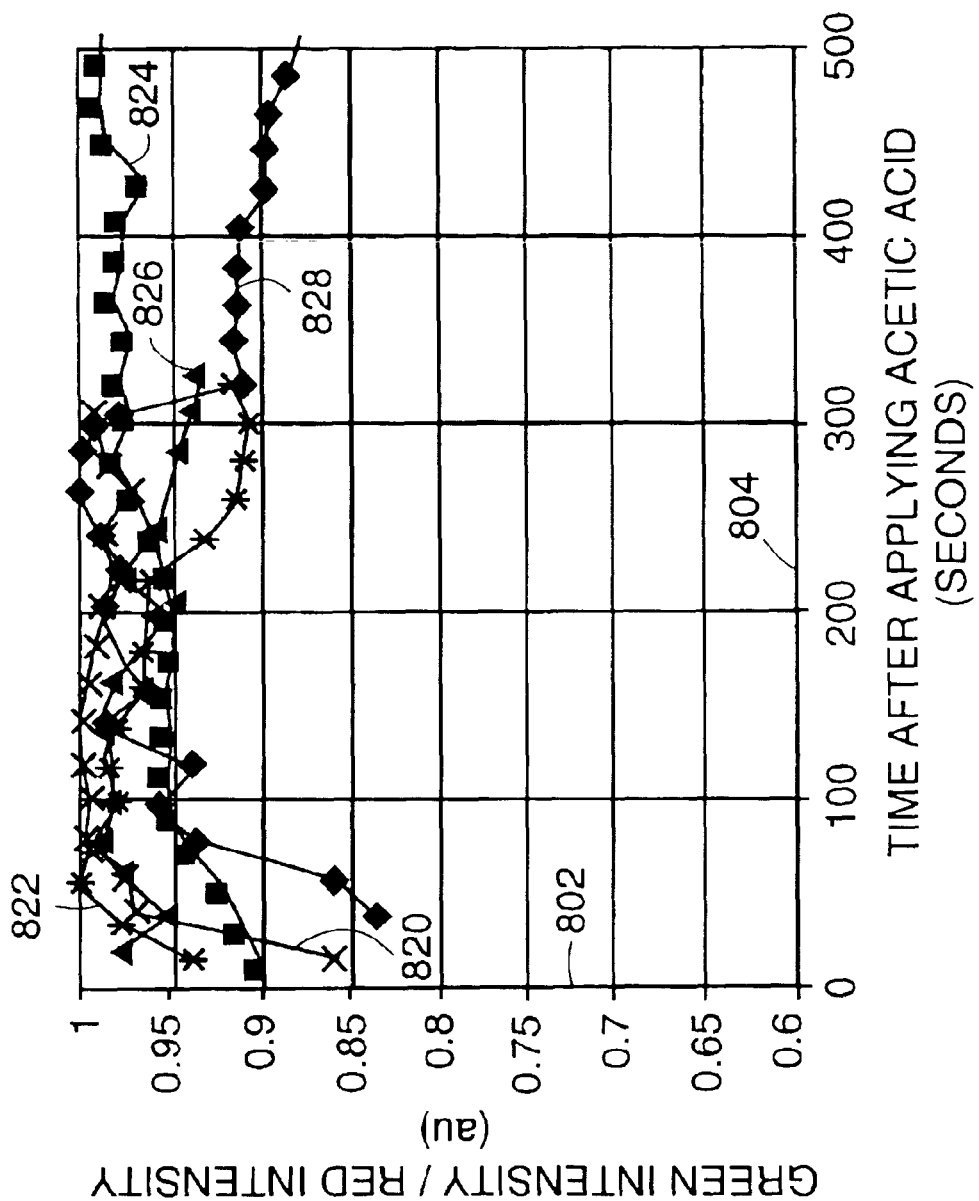
Figure 6C:
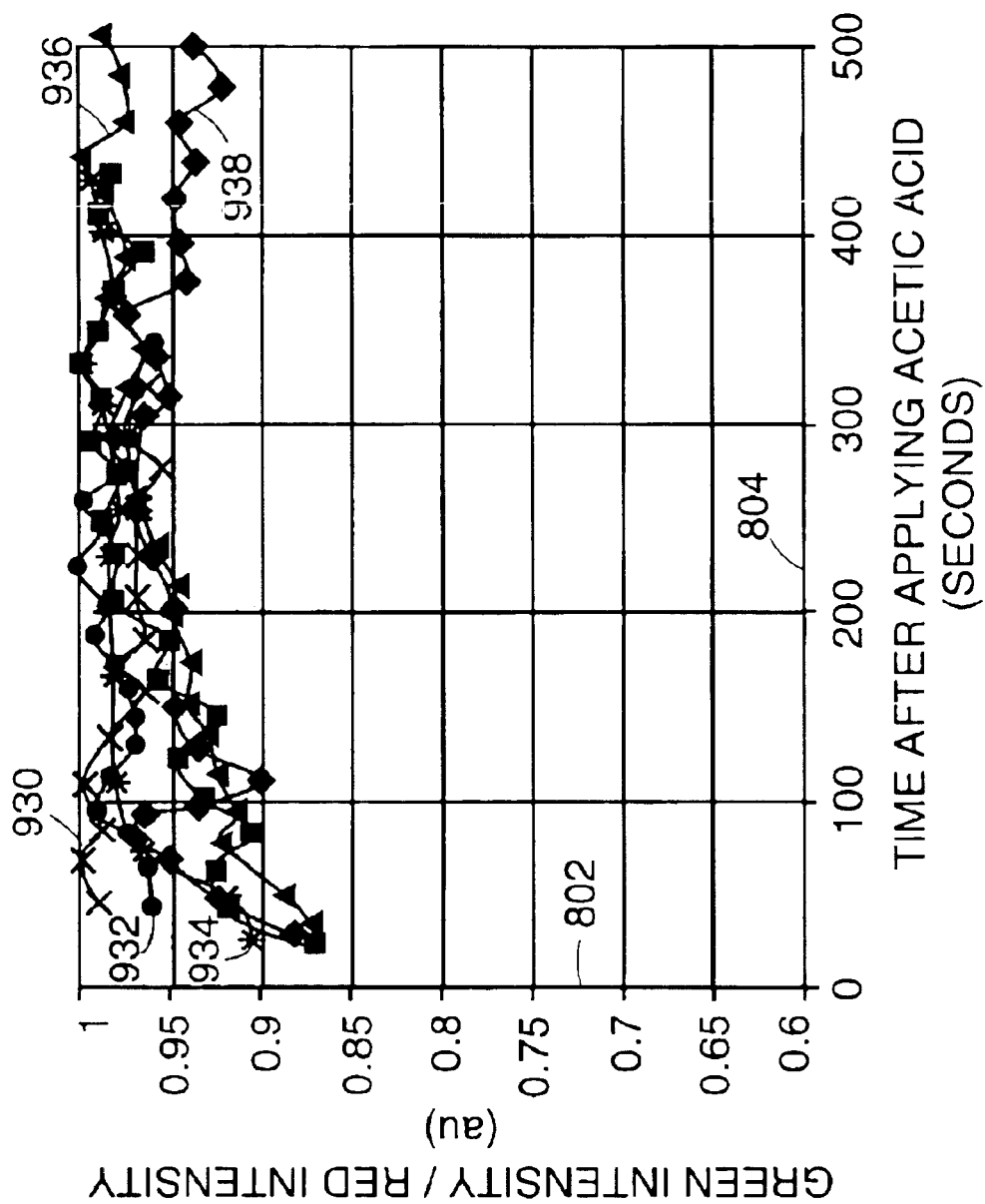

FIGS. 6A–6C are diagrams, generally 800, that show graphs of raw data plotted using the ratio of mean green intensity to mean red intensity, normalized to maximum intensity, as the vertical axis 802 (expressed in arbitrary units), and using the time after appllication of acetic acid to the tissue, expressed in seconds, as the horizontal axis 804. FIG. 6A is a diagram that shows the raw data of ROIs correlated to CIN II/III lesions, as curves 810, 812, 814, 816, 818 representing observations taken from five individuals. FIG. 6B is a diagram that shows the raw data of ROIs correlated to CIN I lesions, as curves 820, 822, 824, 826, 828 representing observations taken from five individuals. FIG. 6C is a diagram that shows the raw data of ROIs correlated to normal mature squamous tissue, as curves 830, 832, 834, 836, 838 representing observations taken from five individuals.

An operator of the illustrative system and method defines a region of interest on an image. The intensity readings of the pixels in this region are averaged to provide a quantitative value of brightness as recorded through the particular filter (or unfiltered). By plotting these values as functions of time, a picture of the evolution of the acetowhitening at the selected location in the image is created.

Figure 7:
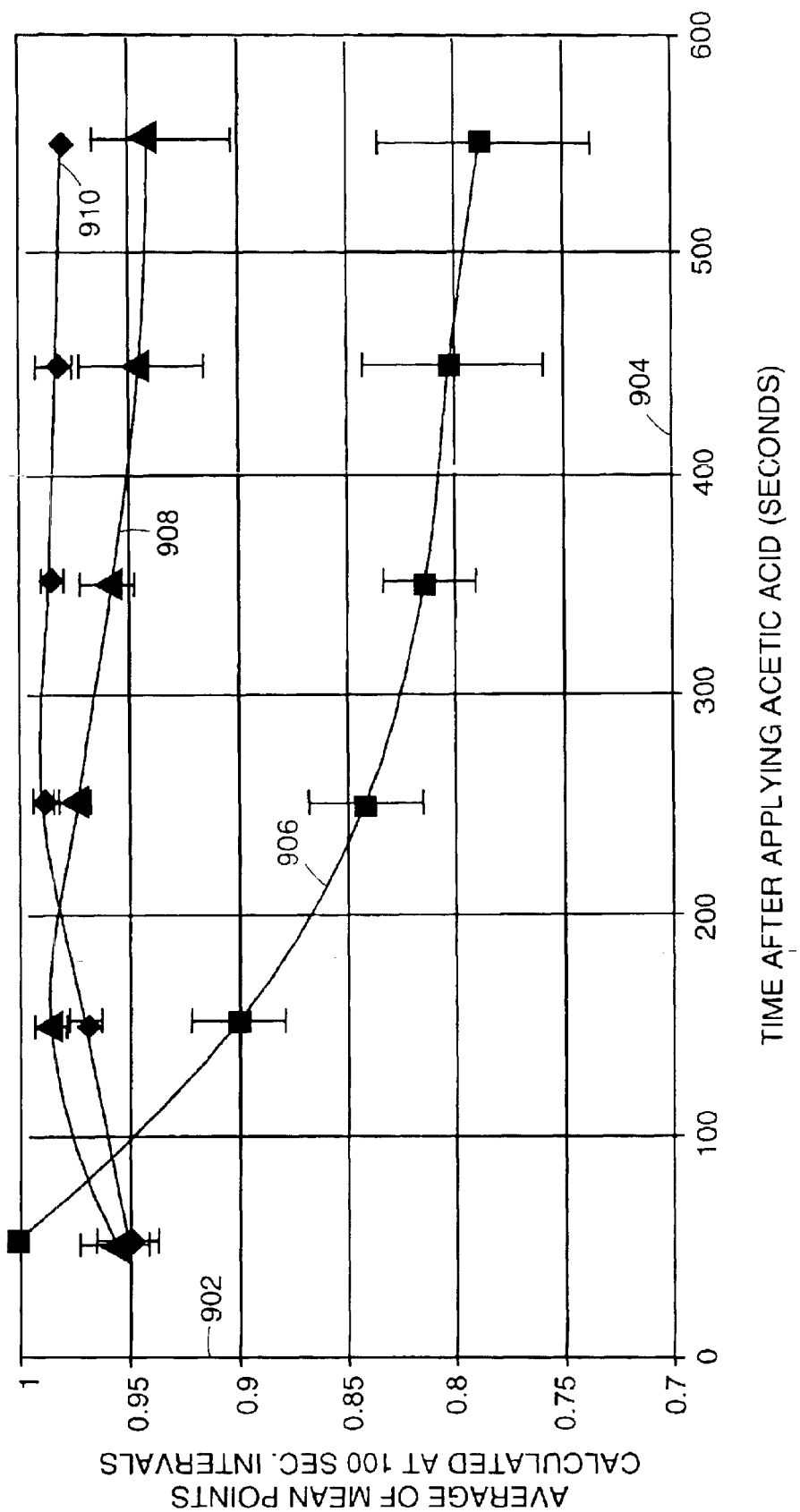
FIG. 7 is a graph showing curves representing averages of data processed according to principles of the invention.

A clinically useful tool based on the acetowhitening kinetic characteristics analyzes the data to differentiate CIN II/III lesions from CIN I lesions and normal mature squamous tissue. According to one illustrative embodiment, the technique uses mean values from 100 second segments of individual patient kinetic curves. The curves are processed by calculating the mean of segments along the curve, i.e. the mean value of the data in the temporal range from about 100–200 seconds after application of the chemical agent, the mean value of the data in the temporal range from about 200–300 seconds after application of the chemical agent, and so forth. FIG. 7 is a graph 900 showing curves of the averages of data processed in this manner, in which the average values are plotted along the vertical axis 902 (expressed in normalized units), and using the time after application of acetic acid to the tissue, expressed in seconds, as the horizontal axis 904. The curve 906 represents data relating to CIN II/III lesions. The curve 908 represents data relating to CIN I lesions. The curve 910 represents data relating to mormal mature squamous tissue.

Figure 8:
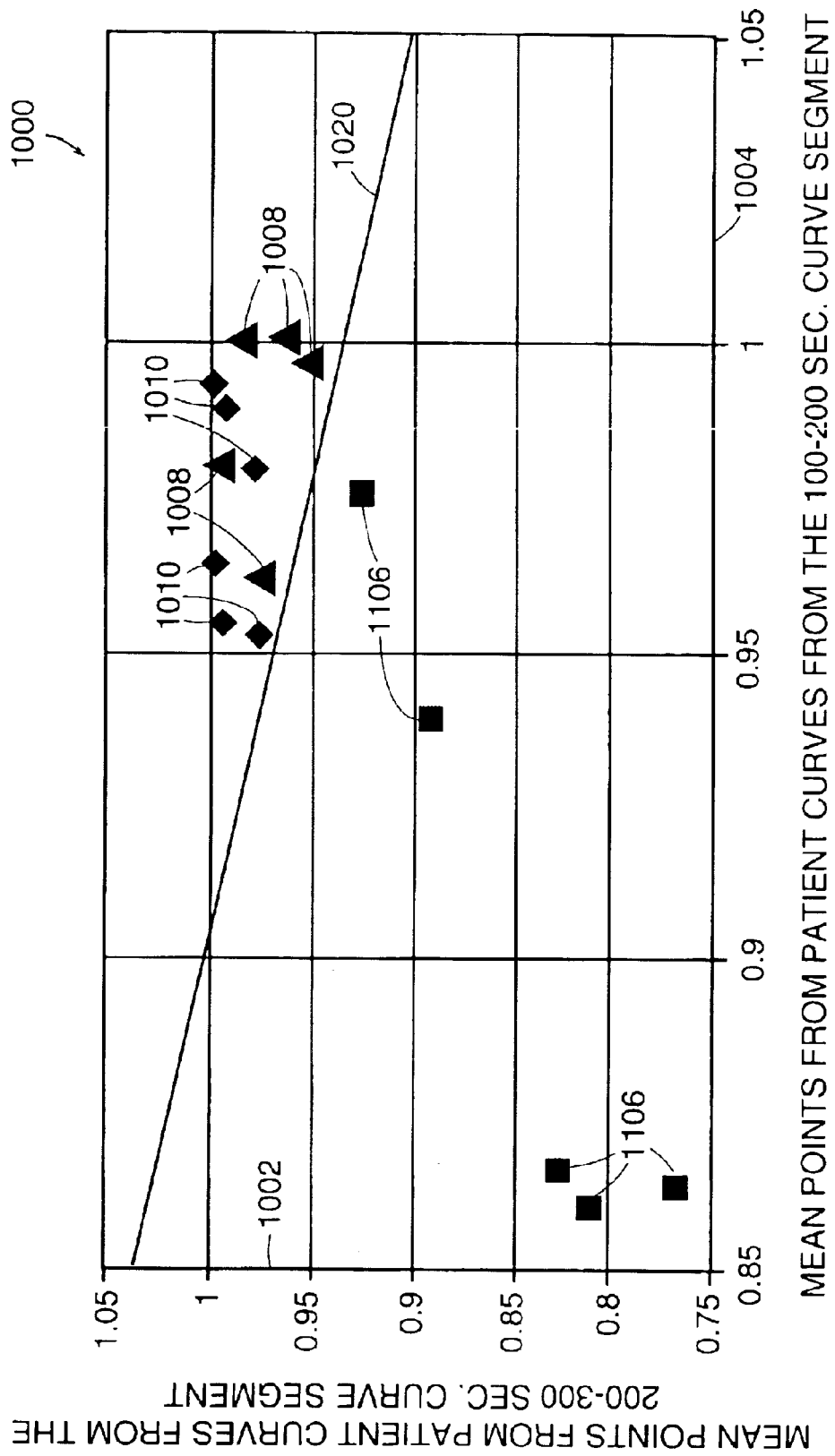
FIG. 8 is a graph plotting computed ratios that show a basis for differentiating CIN II/III lesions from CIN I and normal tissue for individual specimens, according to principles of the invention.

FIG. 8 is a scatter plot 1000 generated by taking the ratio of mean values from two time intervals (100–200 seconds) and (200–300 seconds) for data from individual specimens. In FIG. 8, the average values for the time interval 200 seconds to 300 seconds (expressed in normalized units) are plotted along the vertical axis 1002, and the time interval 100 seconds to 200 seconds (expressed in normalized units), is plotted as the horizontal axis 1004. The points 1006 represent data relating to CIN II/III lesions. The points 1008 represent data relating to CIN I lesions. The points 1010 represent data relating to mormal mature squamous tissue.

FIG. 8 shows a basis for differentiating CIN II/III for individual specimens. An illustrative line 1020 is a line of demarcation between the CIN II/III data and the remaining data. A second technique using the first derivative of the curves shown in FIG. 7 is also operative. This technique yields similar results to those shown in FIG. 8.

According to another illustrative embodiment of the invention, an indication of the presence or lack of cancerous or precancerous tissue is obtained by recording the optical response in two parts of the visible spectrum. In this embodiment, the inventors have observed that at short wavelengths, such as 380 nm, absorption by hemoglobin can reduce signal intensities. Optical responses are recorded in that part of the spectrum where optical response variation can be detected due to morphological changes in tissue which are associated with cancerous and precancerous tissue, such morphological variations having a strong impact on light scattering. At longer wavelengths, beyond 590 nm and to about 750 nm, scattering of light from cancerous tissue was substantially greater than from normal tissue, and thus the reflected responses from cancerous tissue in that spectral range were greater than from normal tissue.

It is desirable to standardize the responses from the tissue using a signal at a wavelength where both of these influences are relatively weak. In one embodiment, the system of the invention standardizes responses at 480 nm for this purpose. In one embodiment, the response, e.g., the observed reflectance, is recorded at three wavelengths, and the responses obtained at the short wavelength (between 360 and 440 nm) and at the long wavelength (between 590 and 750 nm) are divided by the response at 480 nm. According to one illustrative methodology of the invention, normalized reflections at longer wavelengths indicate cancerous and precancerous tissue, while lower intensity normalized refeflections indicate healthy tissue. According to a further illustrative methodology of the invention, reflections in the short wavelength part of the spectrum indicate cancerous and precancerous tissue, while higher intensity reflections indicate healthy tissue.

An algorithm using the rate of change of white light reflection at some specific wavelength, for instance, at 600 nm, can provide accurate differentiation between pathologic and healthy tissue within the first 60 seconds after the application of a pathology differentiating agent like acetic acid. Other algorithms, using both the aforementioned rate of change, or the time lapsed to reach maximum back scattering after application of a differentiating agent, or the time required to attain specific back scattered (normalized) threshold values, permit the diagnosis of the presence or absence of cancer in the screened cervix.

As an aspect of the invention, methods are provided that employ specific algorithms to analyze the back-scattered responses obtained at the preselected wavelength or wavelengths either with or without a chemical agent. Algorithms further provide for classifying examined tissues as normal or pathological. In certain embodiments, these systems are characterized by ease of operation, simplicity and ruggedness.

Figure 9:
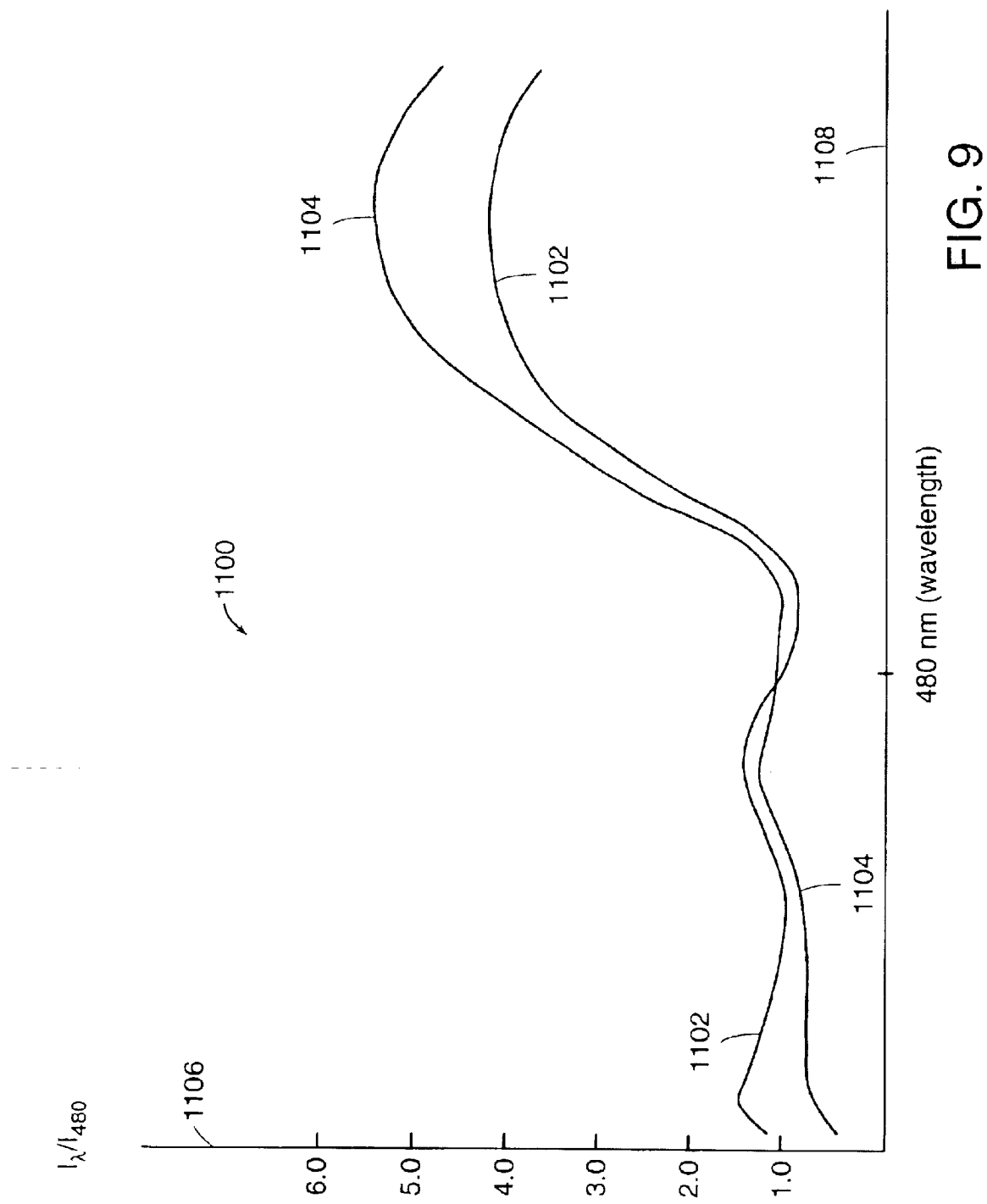
FIG. 9 is a graph showing responses, normalized at 480 nm, from tissues as function of wavelength, according to principles of the invention.

FIG. 9 presents a graph 1100 showing two data curves 1102, 1104 obtained from healthy (no evidence of disease, or NED) and cancerous (CIN) tissue respectively. Normalized intensity is plotted along the vertical axis 1106 and wavelength (in units of nm) is plotted along the horizontal axis 1108. All received responses ($I_\lambda$) are normalized by dividing the intensities received by the intensity obtained at an arbitrary wavelength. Reflections measured at 480 nm are used for this purpose, since it is in a part of the spectrum where the responses' intensities are relatively independent of the tissue state (healthy or pathological). FIG. 9 shows that the received intensities at longer wavelength (between 550 to 750 nm) are consistently higher for cancerous tissue (curve 1104) than for healthy tissue (curve 1102). The data indicate that the use of three wavelengths from the reflected spectrum of tissue provides correlation between the presence or absence of cancer in the target tissue.

In one embodiment, an algorithm utilizes the reflected reading from the tissue at the three selected wavelengths to produce an indicator of the presence or absence of a pathology in the target tissue, or to create an artificial pathology image of the tissue observed. In the first step of the algorithm, the responses are collected at three wavelengths for each point observed. In one embodiment, the following three wavelengths can be used:

$\lambda_1 = 380$ nm
$\lambda_2 = 480$ nm
$\lambda_3 = 650$ nm

It is understood that one can select wavelength ranges rather than specific narrow bands as illustrated here. Normalized reflected intensities may then be defined:

$R_{380} = I(\lambda_1)/I(\lambda_2)$
$R_{650} = I(\lambda_3)/I(\lambda_2)$ where $I(\lambda_1)$, $I(\lambda_2)$ and $I(\lambda_3)$ are the measured reflected intensities at $\lambda_1$, $\lambda_2$ and $\lambda_3$ respectively. These normalized intensities $R_{380}$ and $R_{650}$ (which are dimensionless), can vary from about 0.2 to about 6. In one embodiment, the intensity of the reflected light at 380 and 650 nm are normalized, where the normalization parameter is the reflected intensity at 480 nm. It should be evident to those of ordinary skill in the art that while in one embodiment $R_{380}$ is defined at $\lambda = 380$ nm and $R_{650}$ at $\lambda = 650$ nm, one can define R(low $\lambda$) and R(high $\lambda$) around neighboring wavelengths in the respective ranges as well, using data such as presented in FIG. 9 from a number of subjects and tissue with varying pathologies in those subjects as a "training set" to calibrate the apparatus being employed. The selection of the "bandwidth" around the center wavelength is related to the kind of instrumentation selected for the actual device, as described below in more detail.

As long as the bandwidths selected during the calibration or training of the device and its subsequent use in the field for screening purposes are the same, good correlation is found between high values of $R_{650}$ coupled with low values of $R_{380}$ and the presence of cancerous and precancerous, or CIN, tissue. Similarly, good correlation is found between low values of $R_{650}$ and high values of $R_{380}$ and the presence of healthy, or NED, tissue. Specifically, for cervical tissue that when $R_{650} < 3.1$ and $R_{380} > 1.1$, the tissue is healthy (NED) and when $R_{650} > 3.3$ and $R_{380} < 0.9$ the tissue is cancerous or precancerous (CIN of all grades).

In one embodiment, a grading algorithm is incorporated in a data processing unit employed by these systems and methods. The grading algorithm utilizes the pair ($R_{650}$, $R_{380}$) and classifies the reflections from each site observed into three groups. In the case of cervical tissue, the algorithm classifies reflections for which the pair obeys $R_{650} < 2.9$, $R_{380} > 0.1.1$ as "healthy tissue" or NED. Similarly, a second group of sites, for which the pair obeys $R_{650} > 3.5$, $R_{380} < 0.9$ is classified as cancerous or precancerous tissue or CIN. Finally, a third group of tissue, including those tissues for which the reflections pairs obey the relationships $2.9 < R_{650} < 3.5$, $0.9 < R_{380} < 0.1.1$, is classified as tissue for which a determination cannot be made. An algorithm according to these systems and methods classifies each point in the observed tissue as healthy or unhealthy. If this classification can not be performed for a particular tissue area, that area is segregated into a third, "unclassifiable" class.

An algorithm according to these systems and methods maps tissue for the presence or absence of a pathology. In one embodiment, an algorithm utilizes an independently determined set of threshold values for $R_{380}$ and $R_{650}$. These threshold values are determined in clinical studies from a large number of patients from which both readings of $R_{380}$ and $R_{650}$ are compared with biopsies taken from the tissues from which these values are determined. The threshold values as well as the actual wavelengths where the reflections are taken (and the normalizing wavelength utilized to determine from $I(\lambda)$ the normalized reflection $R_\lambda$) can vary from the values presented herein, as long as the short wavelengths reflections correlate well with absorption by hemoglobin and the long wavelengths reflections with variations of scattering between healthy and pathological tissues.

The wavelengths presented in the example above and shown in FIG. 9 are useful in the diagnosis of cervical tissue abnormalities. It is understood, however, that other wavelengths may be useful, particularly when other tissue areas are studied. Furthermore, the critical threshold values of the short and long wavelengths standardized reflections, R, are subject to determination for each type of tissue targeted.

In another embodiment of the invention, a tissue integral algorithm is used, where the cervix as a whole is examined to determine if a pathology exists without actually obtaining an image of the location of such pathology within the tissue. This algorithm is used as follows. The computer 650 collects the normalized reflection $R_{650}$ for all measured sites on the tissue and determine the minimum $R_{650}(min)$ of the set $\{R_{650}\}$. The computer 650 determines the maximum value $R_{650}(max)$ of the set $\{R_{650}\}$. In one embodiment, if the condition $R_{650}(max)<1.2R_{650}(min)$ of the set $\{R_{650}\}$ is true (e.g., if all observed values of $R_{650}$ are smaller than 120% of the smallest value of $R_{650}$ $R_{650}(min)$), then the tissue is free of pathology. If this condition is not met, pathology of some type is indicated, and the subject should be referred for additional diagnostic tests to identify the type and location of the suspected cervical pathology.

A similar algorithm involving $R_{380}$ can be used, whereby the computer 650 determines the minimum $R_{380}(min)$ of the set $\{R_{380}\}$, for the normalized reflection $R_{380}$ observed for all tissue locations. The computer 650 determines the maximum value $R_{380}(max)$ of the set $\{R_{380}\}$. In one embodiment, if the condition $R_{380}(max)<1.20R_{380}(min)$ of the set $\{R_{380}\}$ is true, (e.g., if all observed values of $R_{380}$ are smaller than 120% of the smallest value of $R_{380}$, $R_{380}(min)$), then the tissue is free of pathology. If this condition is not met, pathology of some type is indicated, and the subject should be referred for additional diagnostic tests to identify the type and location of the suspected cervical pathology.

It is understood that an algorithm in which both of the above conditions are met also results in a valid classification of the subject population into healthy and possibly pathological tissue. It should further be clear that an algorithm based on simultaneously satisfying both conditions can be a useful grading system of tissue for the presence or lack of pathology. Such an algorithm can be expected to result in a greater number of "undetermined" cases. However, the confidence level of correctly grading healthy and pathologic tissue is higher that when using either one of the tissue integral algorithms described above individually.

It should furthermore be evident to those of ordinary skill in these arts that other algorithms can be constructed without departing from the scope of the systems and methods described above but that nonetheless rely upon the fact that scattering from non-pathological tissue at wavelengths between about 600 nm and about 750 nm is consistently greater for pathological tissue than for healthy tissue, or that rely upon the fact that absorption of light in the range of about 370 nm to about 430 nm is greater for pathological tissue than for healthy tissue. Such algorithms, consistent with these systems and methods, are useful in classifying a subject's cervix for the presence or lack thereof of pathological tissue (e.g., a state of health of a subject's cervix). In other embodiments, algorithms can employ data collected at other wavelengths in order to diagnose pathologies of the cervix or pathologies of other body tissues.

Figure 10:
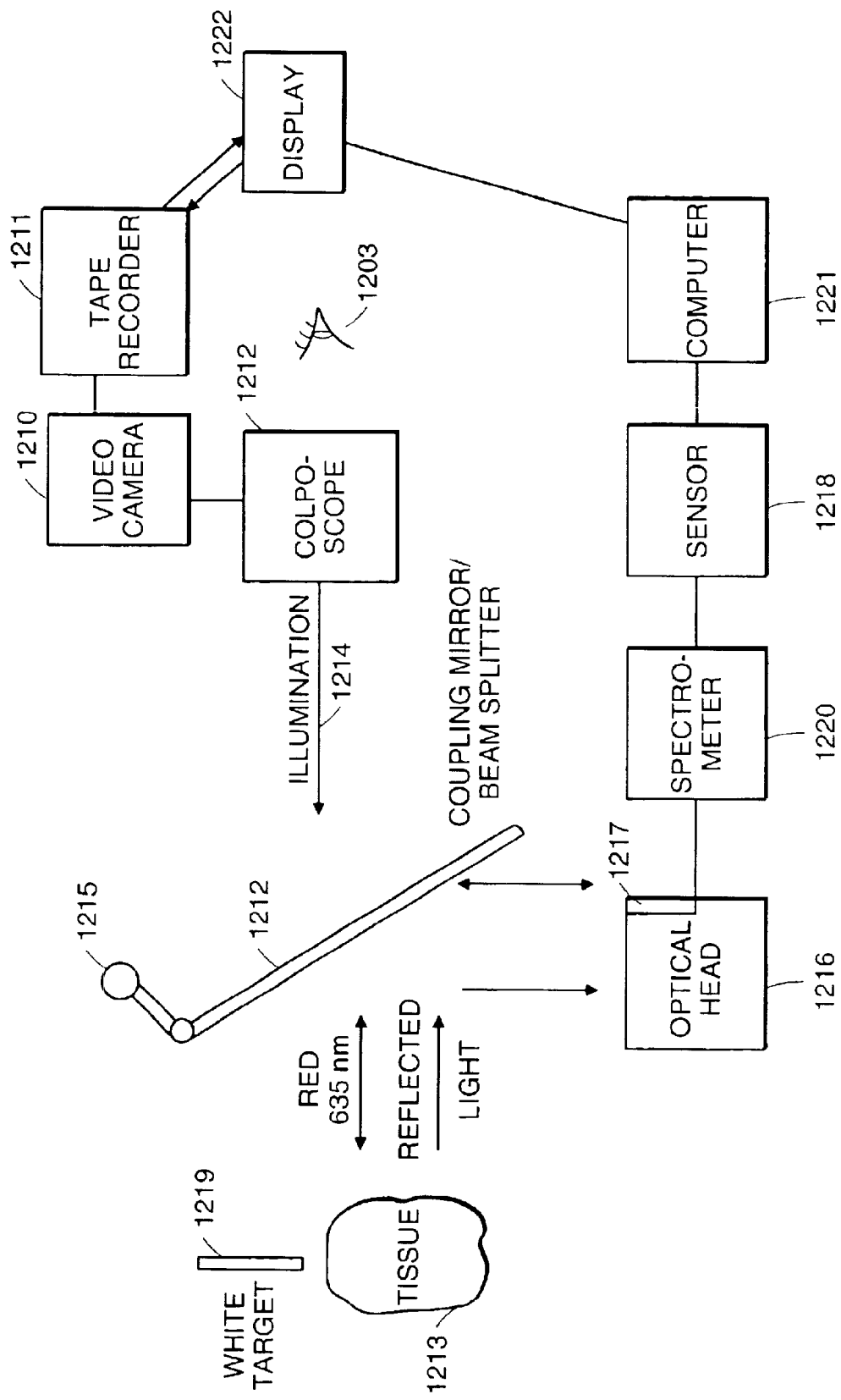
FIG. 10 is a functional block diagram of an embodiment of a another illustrative system useful for monitoring the effects of a chemical agent on a specimen according to the invention.

FIG. 10 shows an illustrative embodiment of a device for determining the presence or absence of pathology in a tissue of the cervix according to the invention. In this figure, a screening device (shown generally at 1200) is an integral part of a colposcope 1202, and is used to make determinations of tissue pathology point by point. A colposcope 1202 is provided with a high intensity light source and optics to view cervical tissue, all included within the colposcope 1202. The image viewed by an observer 1203 is recorded with a video camera 1210 and recorded for future reference on magnetic media through a video tape recorder 1211. The instrument depicted in FIG. 10 is used for determining the presence or absence of pathology point by point. Since it is paired with a colposcope 1202, this embodiment is suitable for use by highly trained professionals, such as gynecologists. A beam splitter 1212 is used to select a site in the target tissue 1213 which is illuminated with white light 1214 from the light source provided in the colposcope 1202. The position control of the beam splitter (and thus selection of the point examined in the target tissue) is accomplished with a "joystick" 1215. The optical head 1216 includes a small laser diode (wavelength at about 635 nm) 1217, having a beam coaxial with the optical head's detection optics. In operation, the red beam is pointed toward the tissue 1213. Since the optical axis of the laser diode 1217 and the collection optics in the optical head 1216 are the same, the optical head 1216 measures the light reflected from the point illuminated by the red laser diode beam. In order to maintain the calibration of the optical head's sensor 1218, a white reflector 1219 is provided within the illumination path of the colposcope, to which the operator directs the seeking beam from the laser diode 1217. The reflectance from the white reflector 1219 is used as a standard for calibrating the sensor 1218. Such a white reflector can be made from Spectrolon™, from Labsphere Corporation. Alternatively, high purity $BaSO_4$ reflecting paint from the Kodak Corporation can be applied to a flat surface and used.

In some embodiments of the invention, a polarizer is interposed in the back scattered beams which considerably reduces the specular reflection from the target tissues. The specular reflection is understood to comprise the light reflected from the thin film of moisture overlaying the target tissue that has not interacted with the underlying tissue.

In operation, the physician directs the beam 1214 to a specific site on the suspected tissue 1213. The reflected light from this site is collected by the optical head 1216. A spectrometer 1220 (which can be either a refractive or dispersive spectrometer) disperses the light so that the intensity of the reflected light at preselected wave lengths can be measured in the detector 1218. In one illustrative embodiment, three preselected wavelengths are chosen. In certain embodiments, the sensor 1218 comprises a plurality of sensors corresponding in number to the number of preselected wavelengths, so that one sensor is dedicated to each wavelength. The sensor 1218 can be an ICCD, a standard CCD, or any other detector system known in the art or envisioned by those of ordinary skill in these arts.

Data from the sensor 1218 is analyzed in a computer processor 1221 by applying an algorithm system as described above, and a score is obtained from the data processing that relates to the presence or absence of pathology at the tissue area being illuminated by the laser diode 1217. This score is graphically represented on a display 1222. The digital information corresponding to the score is made available electronically for further processing or representation. In certain embodiments, points for which pathological scores are obtained can be represented on a display 1222 as superimposed upon an image provided by a video camera 1210. In one embodiment, abnormal points are identified graphically with an artificial color not commonly found in cervical tissue, such as shades of green. It will be seen below that other embodiments provide for creation of artificial images or representations of pathologies. The embodiment illustrated in FIG. 10 is suitable for operation by a gynecologist in conjunction with colposcopy. In this setting, the device is well adapted for use as an assisting device for determining which areas of the cervix may require biopsies.

In one embodiment, the systems and methods of the invention provide a hand held device adapted for illuminating a target tissue with white light and further adapted for detecting reflections or backscattered responses at three specific wavelengths. FIG. 11 shows an illustrative embodiment suitable for screening applications. This embodiment provides features of a visualization colposcope and features of a screening device according to the present invention. In this embodiment, a superimposition of pathological findings on a cervical image may be produced.

FIG. 11 shows a colposcreener 1330 consisting of two orthogonal optical paths 1331 and 1332. The first optical path 1331 includes a plurality of lenses (for example lenses 1333, 1334 and 1335) to image the tissue 1336 so that it can be viewed by an observer 1303. The second optical path 1332 includes a distal portion 1331a of the first optical path 1331 (for example lenses 1334 and 1335), a beam splitter, 1338 and additional lenses (for example, lenses 1337 and 1339). The beam splitter 1338 couples the two optical paths 1331 and 1332 to the distal portion 1331a of the first optical path 1331, directing half of the light reflected back from the tissue 1336 to be viewed by the observer 1303 through the ocular 1333 and directing half to a sensor 1340. The sensor 1340 is coupled to the optics via a mirror 1341, as shown in FIG. 11, or the sensor 1340 is positioned in the image plane of the second optical path 1332. In some embodiments, the sensor 1340 comprises a plurality of sensors corresponding in number to the number of preselected wavelengths, so that one sensor is dedicated to each wavelength. The sensor 1340 can be, for example an ICCD, a standard CCD, or any other detector system known in the art or envisioned by those of ordinary skill in these arts. A filter wheel 1342 is placed in the optical path of the detected beam 1332, to allow at any given time only one wavelength to reach the detector 1340. The filter wheel 1342 is mounted on an appropriate driving mechanism, for instance, a stepper motor 1343, which sequentially indexes the wheel to the appropriate filter.

Arrangements of filter wheels are shown in more detail in FIGS. 12A, 12B and 12C. In one embodiment, as shown in FIG. 12A, the filter wheel 1442 has three filters, 1444, 1445 and 1446, each capable of blocking most of the spectrum of the reflected beam except around the three selected wavelengths, 380 nm, 480 nm and 650 nm respectively (for the filters 1444, 1445 and 1446). It will be understood by those of ordinary skill in the art that a number of duplications of these filters can be employed for drive simplicity, in particular when the cross section of the reflected beam is narrowed (at the common focal point of the lens on both sides of the filter wheel 1442), so as to allow more than three wavelengths to be determined per rotation of the filter wheel 1442. In such an arrangement in the illustrated embodiment, the number of filter slots would be a multiple of three. In another embodiment, as shown in FIG. 12B, a different filter wheel, 1447, is used in place of the previously illustrated filter wheel 1442. The filter wheel 1447 has four positions (or multiples of four). The first three, positions 1448, 1449 and 1450, are filters transmitting at 380 nm, 480 nm and 650 nm respectively, as cited above, and a fourth slot, 1451, being spectrally neutral, namely it is either a simple open slot in the filter wheel 1447, or a neutral filter that reduces the transmission of all wavelengths by a constant factor. The latter case simplifies the task of maintaining the signals received by the sensor 1440, (for instance a CCD) under a given threshold and thus preventing sensor's saturation.

In one embodiment, the shape of the colposcreener 1330 is similar to the device depicted in FIG. 11. FIG. 11 shows a colposcreener 1330 shaped like a gun, with a trigger 1352 used to initiate the processes of obtaining optical reflection data and viewing the tissue 1336. In operation of this embodiment, pressing the trigger 1352 switches on a light source in the control console 1353. This light source is concentrated into an optical fiber bundle (not shown) included in the control cable 1354 which connects the control console 1353 and the colposcreener 1330. The optical fiber bundle 1354 delivers light to the distal end 1355 of the colposcreener 1330. In one embodiment, a cone of white light 1357 illuminates the target tissue 1336 homogeneously. It is understood that other shapes and configurations of the colposcreener 1330 may be envisioned by those of ordinary skill in these arts without departing from the scope of the systems and methods disclosed herein. Furthermore, while the colposcreener 1330 is adapted for examination of the cervix, other shapes and embodiments consistent with these systems and methods may be devised that are structurally adapted for other anatomic areas.

FIG. 11 further shows that light reflected from the tissue is split by the beam splitter 1338 into a viewing beam carried along the optical path 1331 and a detection beam carried along the optical path 1332. In that manner, the tissue screened is viewed directly through the ocular 1333 while the detection beam is being sequentially scanned for the three wave length discussed above. The tissue is imaged onto the sensor 1340. In one embodiment the sensor 1340 comprises a CCD array, whereby the light intensity reflected for each point in the tissue is measured. The data from the sensor 1340 is transmitted through a data cable 1356 to a data processing unit 1358 for further analysis. Synchronization signals generated in the control console 1353 provide correct indexing of the streams of data for each one of the three filters in the filter wheel 1342. This may be achieved by using the signal sent to the stepper motor 1343 to coordinate with the data stream from the sensor 1340.

In one illustrative embodiment, the synchronization task is simplified by using the geometry of the filters in the filter wheel 1342. In this embodiment, the motor 1343 is used in a continuous rather then a stepping manner, thus the filter wheel 1342 rotates continuously. An embodiment using a filter wheel in this way is shown in FIG. 12C, where the filter wheel 1459 is depicted as having three unequal filters 1460,

1461 and 1462, separated by unequal spaces 1463, 1464 and 1465. In this embodiment, a CCD or a CCD array is advantageously employed as the sensor 1340, as previously described. Since the CCD has its highest sensitivity in the red part of the spectrum, and the light source is typically richer in the red part of the spectrum as well, the 650 nm red filter 1460 in FIG. 12C is much shorter, with shorter collection time. The short collection time is used to indicate to the data analysis unit 1358 that the red filter 1460 (transmitting selectively at 650 nm) is being used. To better equilibrate the intensities received, the green filter 1461 (transmitting selectively at 480 nm) is larger than the red filter 1460. The blue filter 1462 (transmitting selectively at 380 nm where the CCD is least sensitive) occupies the longest segment of the circumference. The signals received at various wavelengths are more homogeneous and easier to analyze. Integration times can be adjusted accordingly. The adjustment of the integration time can be keyed on the "No signal" periods between the filters, represented by the unequal spacings 1463, 1464 and 1465 between the filters.

In this illustrative approach, the actual normalized intensities, $R_{380}$, $R_{480}$ and $R_{650}$ as discussed above are modified to account for the time variability of data acquisition between the three different filters. Since these factors depend on the specific integration time selected, the normalized reflections $R_\lambda$ provided above are used, understanding that algorithms based on these findings are devised once a calibration for a specific design is available.

The data received for each one of the three filters is analyzed for each pixel and is displayed on the display monitor 1322 in a dual fashion. The first display generates a Red/Green/Blue image of the tissue by taking the raw data (normalized for spectral differences in the CCD sensitivity as well as variations of integration times when using the filter wheel 1559 shown in FIG. 12C) from each CCD's pixel and presenting it as a normal full color picture. This is achieved with well known "frame grabbing" electronics readily available commercially.

Each pixel, $P_{ij}$, has associated with it three values (residing in the grabbed frame), $I_{ij,380}$, $I_{ij,480}$ and $I_{ij,650}$, from which are derived normalized intensities $R_{ij,380}$ and $R_{ij,650}$. A strongly discriminating algorithm selects all pixels $P_{ij}$ for which both of the conditions $R_{ij,650}>3.3$ and $R_{ij,380}<0.9$, namely those pixels for which a pathology is identified. These pixels form a group Qij of pathological tissue. A "weaker" discrimination defines as "pathological" only those $P_{ij}$ for which $R_{ij,650}>3.3$ and the so defined $Q_{ij}$ are then painted on the total image as a pathology.

The display superimposes an image of all the pixels $Q_{ij}$ having a "pathological" signature on the natural picture of the tissue. This is achieved by selecting a color uncommon to the tissue (such as green, or blue) and painting said all $Q_{ij}$ (pathological) pixels all in the same color, thus obtaining an artificial-looking image of the extent of the pathology in the tissue. The filter depicted in FIG. 12B wherein one of the positions is a neutral filter uses the image generated by the neutral filter (which will appear on the display having shades of gray) as the background image of the tissue on which the pathology is superimposed in any desired color. To maintain the system of FIG. 11 in calibration, a standard white reflector is used, as described above for FIG. 10.

Figure 13:
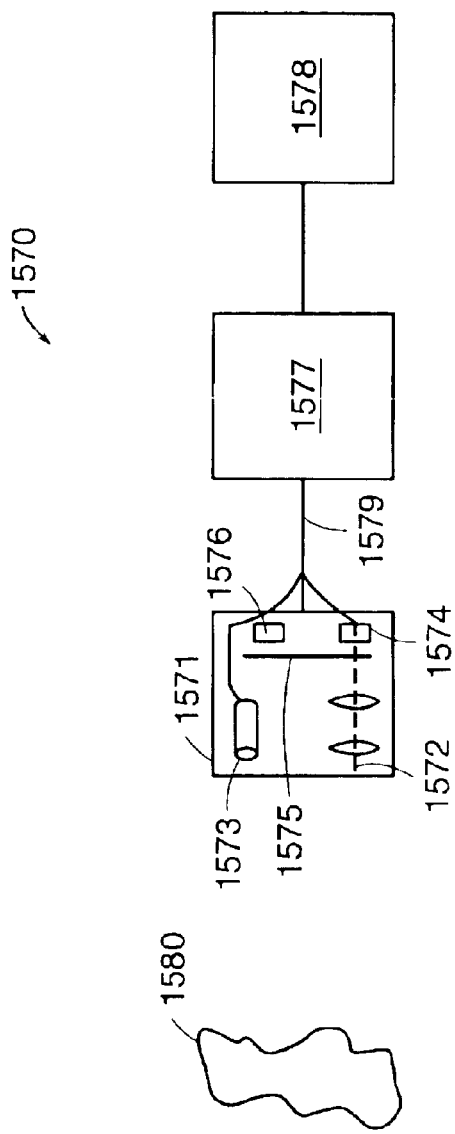
FIG. 13 is a functional block diagram of an embodiment of a system useful for monitoring the effects of a chemical agent on a specimen according to the invention.

FIG. 13 depicts an embodiment in which the apparatus is configured as a screening device 1570 without providing for direct visualization of the tissue being screened by an observer. In the illustrative embodiment, the screening optical head 1571 contains an optical train 1572, an illuminator 1573, a CCD array 1574 and a filter wheel 1575. The filter wheel 1575 is rotated as previously described, either continuously or in a stepping fashion with a stepper motor, 1576. The light source is within the data processing/control console 1577, and the data is displayed on a display 1578. Light from the light source is collected into a bundle of optical fibers 1573 which is an integral part of the cable 1579, between the console 1577 and the screening device 1571. While FIG. 13 shows the optical fibers 1573 as nested within the screening device 1571 at one location, it is understood that the fibers within the bundle can be arranged circumferentially or in any other geometric arrangement in order to provide homogeneous illumination of the target tissue 1580.

Figure 14:
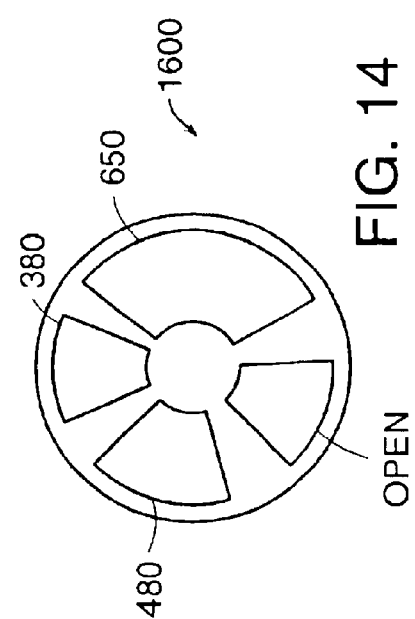
FIG. 14 is a schematic diagram of a filter wheel useful in the system of FIG. 13.

FIG. 14 shows a filter wheel 1600 suitable for use with the device depicted in FIG. 13. The illustrated filter wheel 1600 is configured to select light at wavelengths of 380 nm, 480 nm and 650 nm, with an open area to facilitate synchronization. It should also be evident to practitioners of ordinary skill that any arrangement of filter wheels understood in the art, including those illustrated in FIGS. 12A–12C above, could be used in the depicted system, with the operation of the apparatus being adjusted accordingly.

In operation the screening device 1571 may be pointed to the target tissue 1580. The tissue may be illuminated through the optical fiber bundle 1573 and reflections from the tissue may be recorded by the CCD array 1574 at about 380 nm, about 480 nm and about 650 nm. The data processing unit 1577 analyzes the recorded data using any one of the algorithms described above. Tissues with color enhanced pathologies are represented on the display 1578. In one embodiment of the invention, visual display is not provided and only a reading or printout of the status of the subject (having or nor having a pathology in the target tissue) is presented. In this embodiment, the instrument advantageously uses the above-mentioned tissue integral algorithm. To use this algorithm, the data processing unit 1577, after obtaining the values $R_{ij,650}$ and $R_{ij,380}$ for each pixel $P_{ij}$, determines the maximum and minimum values obtained for $R_{650}$ and $R_{380}$. If the conditions $R_{650}(max)<1.2R_{650}(min)$ and $R_{380}(max)<1.2_{380}(min)$ are met, the subject is classified free of pathologies. Otherwise, the subject is referred for additional diagnostic evaluation to determine the nature and the extent of the suspected pathology.

Figure 15:
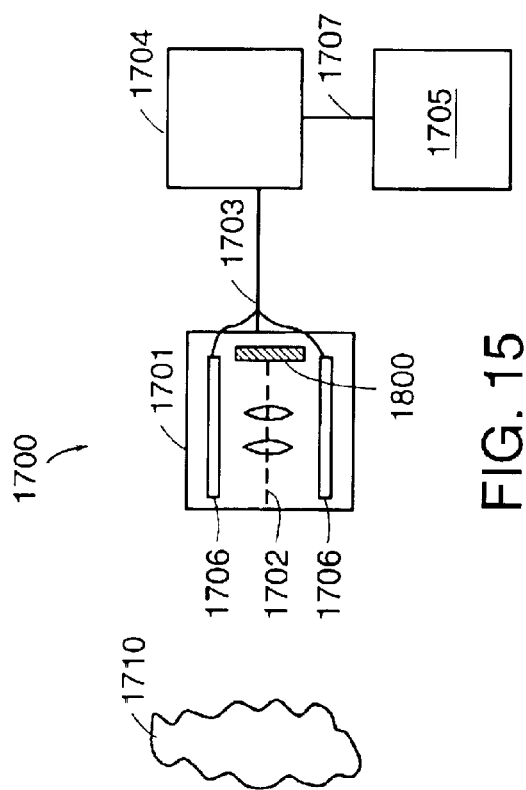
FIG. 15 is a functional block diagram of an embodiment of a system useful for monitoring the effects of a chemical agent on a specimen according to the invention.

In another illustrative embodiment, depicted in FIG. 15, the filter wheel is eliminated. Further, in lieu of a standard CCD array a color CCD array may be used. In the illustrated embodiment, a screening device 1700 includes three modules 1701, 1704 and 1703. The first module, the screening probe 1701, is operably connected to the second module 1704 through a cable 1703. The first module 1701 contains a circumferentially arranged optical fiber bundle 1706 for transmitting light to a target 1710, and an optical path 1702 comprising optical elements for receiving light emitted from the target 1710. The second module 1704 contains a light source coupled to an optical fiber bundle 1706. The fibers in the optical fiber bundle 1706 are distributed circumferentially at the distal end of the probe. Furthermore, the second module 1704 contains a data processing unit, including an electronic frame grabbing submodule to process data received from the color CCD array 1900 in the probe module. Results are displayed on the display module 1705, which is connected to the second module 1704 by way of cable 1707.

Figure 16:
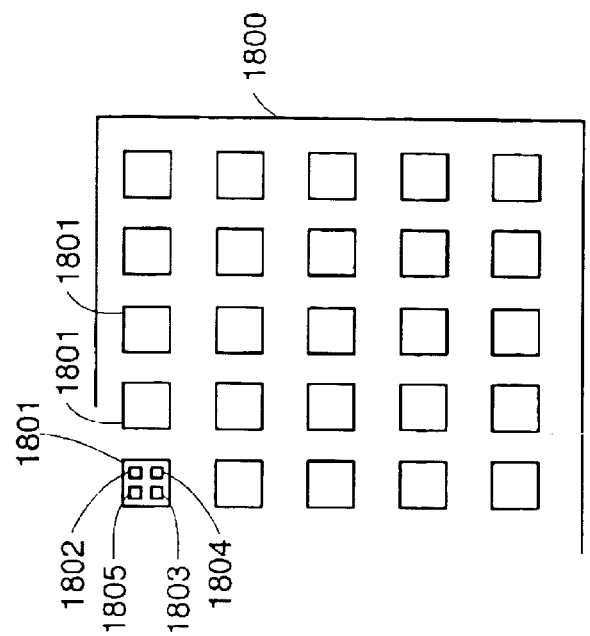
FIG. 16 shows a schematic diagram of a CCD device for use in the system of FIG. 15.

The color CCD array 1900, as used in the illustrated embodiment, may be typically divided into pixels each having four elements. FIG. 16 shows a segment of the surface of such an array 1800. For illustrative purposes, an array of 10×10 elements organized as an array of 5×5 pixels is shown. However, it is understood that such an array can comprise in excess of 500×500 elements and thus more that 250×250 pixels. Each one of the pixels 1801 has two green filters 1802 and 1803, overlaying two of the elements of the four elements in pixel 1801. The other two elements, 1804 and 1805, have respectively a red and a blue filter overlaid thereupon. While the specific filters employed in standard color CCD devices can vary from the three wavelengths selected above, and can vary from manufacturer to manufacturer, standard color CCDs can be used in the invention.

The operation of the device 1700 depicted in FIG. 15 is similar to the operation of the system depicted in FIG. 13, except that no filter wheel is employed. In contrast to the embodiment depicted in FIG. 13, in the embodiment of FIG. 16 the whole image in three chroma is taken at once, and the frame grabbing module transfers the intensities received for each one of the three colors to a data processing device which undertakes the normalization of the long and short wavelength reflection with the middle of the spectrum responses and proceeds to apply to the two artificial intensities so derived any of the previously described algorithms.

In the illustrative embodiment, the system optics 1702 images the target tissue 1710 onto the color CCD 1800, and the signal from each pixel is captured in a frame grabbing device in module 1704. The intensities registered for the two green filtered elements are averaged and used as the normalization value for the intensities registered for the red filtered element and for the blue filtered element. In this fashion, normalized values $R_{ij}(B)$ and $R_{ij}(R)$ are obtained for each pixel having a row i and a column j. These normalized values respectively represent the normalized reflected intensities in the blue and red part of the spectrum.

While the filters used in commercial color CCD do not correspond exactly to the wavelength 380 nm and 650 nm mentioned above, and furthermore the bandwidth of those filters are relatively wide, satisfactory calibration and discrimination between pathological and healthy tissue can be achieved. The threshold values can be changed for R(B) and R(R) relative to those shown above for $R_{380}$ and $R_{650}$. These values vary somewhat depending on the source of the color CCD. To alleviate the problem of variability, an array of filters with the appropriate fixed wavelengths of about 380 nm, about 480 nm and about 650 nm can be overlaid over a standard CCD array to obtain a screening device that has no moving parts (such as the filter wheel) in some of the embodiments mentioned above. The general algorithm $R_\lambda(Max) < \alpha R_\lambda(min)$ where $\alpha > 1$ and is a function of the specific $\lambda$ selected is advantageously employed without undue experimentation by ordinary skilled practitioners in these arts to discriminate between healthy and pathological tissue. .

Figure 17:
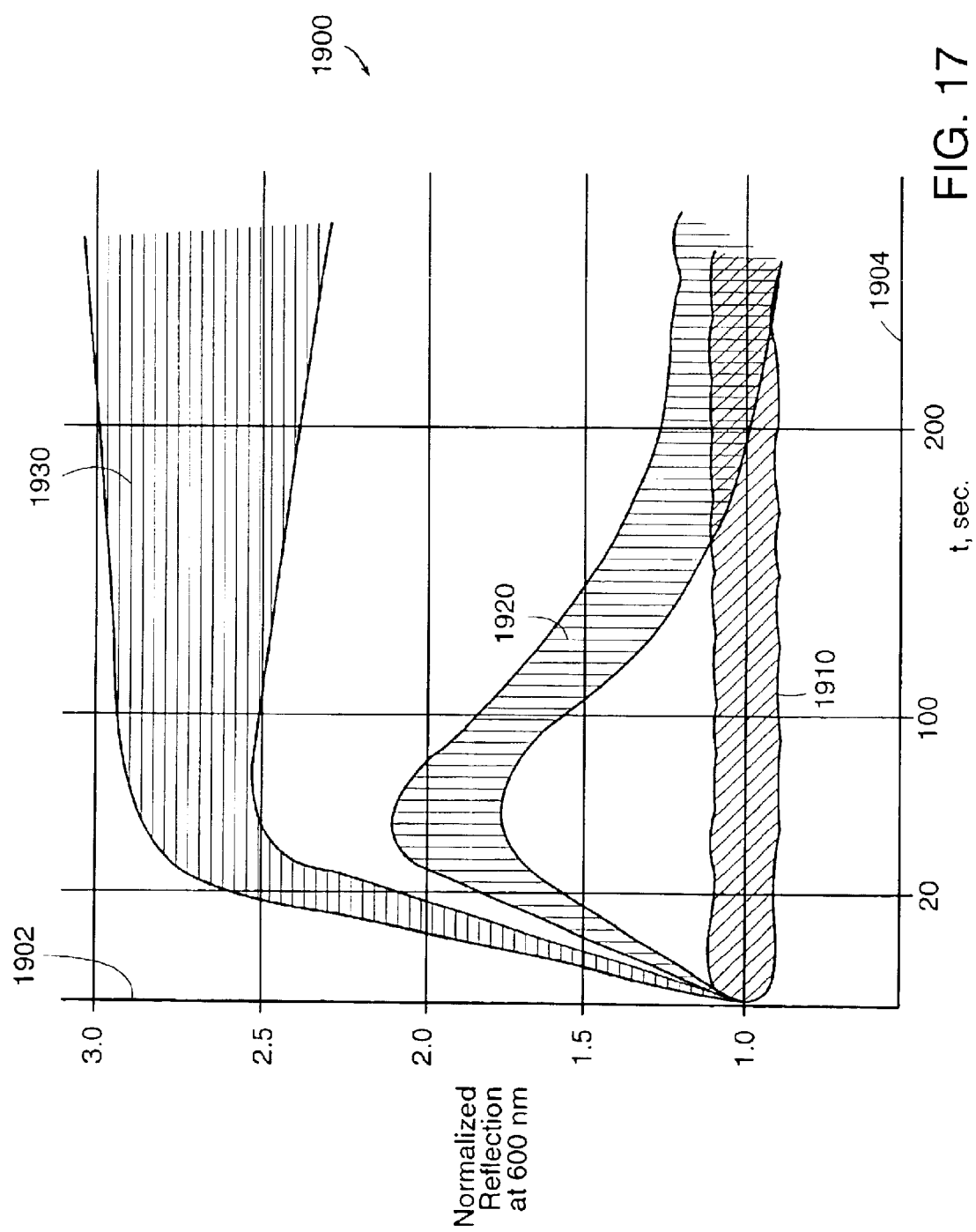
FIG. 17 is a graph showing the time dependence of backscattered responses at 600 nm for various tissue classes (NED, CIN II and CIN III), recorded using systems and methods of the invention.

In another illustrative embodiment, these systems and methods are used in conjunction with an acetic acid delivery system, as shown in FIG. 17. FIG. 17 shows a graph 1900 of measured reflectance I, as normalized by the initial reflectance immediately after the application of the acetic acid, as function of time, beginning with the application of an acetic solution to the cervix, at a wavelength of about 600 nm. The graph 1900 has normalized intensity plotted along the vertical axis 1902 and time expressed in seconds plotted along the horizontal axis 1904. The data collection is achieved by using a single narrow bandpass filter, transmitting around 600 nm, overlaying a CCD. FIG. 17 represents measurements from a number of tissue samples (in vivo, followed by determination of the pathology from biopsies).

The time dependence of the reflected responses from tissues fall into three well differentiated zones. Healthy (NED) tissues have a response 1910 which is independent of time. CIN II tissue shows an increasing response 1920 for about 30 to 60 seconds, and then the reflectance slowly fades out and returns to normal within about three minutes or a little longer. CIN III tissue shows a response 1930 that includes a strong change with time for the first 20 to 30 seconds, and then, the response 1930 stays strong for longer than about three minutes. FIG. 17 shows that the optical behavior of the various tissue classes following the application of the amplifying agent differentiates between healthy and pathologic tissue from measurements taken during the first 10 to 20 seconds after the application of the amplifying agent (or chemical agent), in this case acetic acid.

A useful algorithm employs the rate of change of the normalized intensity I with time, dI/dt at between 10 to 20 seconds after the application of the amplifying agent. According to this algorithm, if $dI/dt < 0.055$ $sec^{-1}$, the tissue is classified as healthy (NED). If $0.075$ $sec^{-1} < dI/dt < 0.11$ $sec^{-1}$, the tissue is classified as CIN II. If $dI/dt > 0.11$ $sec^{-1}$, the tissue is classified as CIN III. In one embodiment, the higher dI/dt during the first 10 to 20 seconds after the application of the acetic acid solution, the more severe the pathology is.

In another embodiment, an algorithm involves the measurement of the normalized reflectance after either 10 or 20 seconds from the application of the acetic acid solution. If I is greater than 1.25 after 10 seconds (or about 1.5 after 20 seconds), the tissue is classified as pathologic, and the patient is directed to have a more detailed analysis of the condition, sometimes, including a biopsy. This embodiment is applied, as an example, when the probe is used in true screening situations rather than in more traditional colposcopic examinations.

In another embodiment, an algorithm is based on the time required to reach a maximum in the back reflected response of the tissue. According to this embodiment, the longer it takes to reach this maximum the more severe the condition, providing, however, that the maximum is more than about 3.0 times the minimum back scattered response for the same tissue. The disadvantage of this approach is that longer exposure may be required, particularly in the case of CIN III, where back scattered responses continue to increase even after more than 200 seconds.

To shorten that time interval, another algorithm compares the maximum normalized response at 600 nm during any interval of time greater than 10 seconds from the application of the acetic acid solution, to the initial response, and if that response is more than 30% larger than the initial response, the tissue is classified as CIN in general. This algorithm is used when fast classification of cervixes in a screening environment is desired.

In yet another embodiment of the invention, a screening algorithm takes an ititial reading of responses for each point probed prior to the application of the acetic acid, stores the values as a standard set, and then takes a number of images sequentially. The screening algorithm performs a point by point subtraction of the value of the stored initial responses from the responses obtained after the application of the acetic acid. The time dependence for various classes of tissue results in distributions similar to those shown in FIG. 17, except that the scale of the back scattered intensities is now changed. The algorithm utilizes the differential responses of various classes in a manner as described above.

Apparatus and methods for controlled delivery amount and delivery pattern of a chemical agent are disclosed below.

Apparatus and method for accurately and synchronously triggering the optical measurements with regard to the time of delivery of the chemical agent are disclosed below. Image capture software to record time-stamped images and user-defined regions of interest to be defined on a master image is disclosed below. This analysis software automates the calculation and display of acetowhitening characteristics from a motion corrected time-sequence of patient images. This improves the ability to correlate instrument measurements to the pathological evaluation of biopsied tissue.

In another embodiment of the invention, when using an amplifying agent such as acetic acid, an automated system delivers the amplifying agent to the target tissue. A triggering mechanism applies the chemical reproducibly and eliminates variability of time delays between the application and the start of obtaining optical responses from the target tissue.

FIG. 18A shows an illustrative embodiment of a system with a screening probe 2000 similar in construction to the probe shown in FIG. 11. This apparatus and the associated techniques are used to improve the demarcation of a start time and to guarantee the application of a constant volume of acetic acid. Another embodiment is a mucosal atomizer device comprising a 3 cc syringe and 6" stylet tubing extension nozzle is used to spray 2 cc of 5% acetic acid uniformly onto the surface of the cervix. The distal part 2013 of the probe 2000 is covered with a composite disposable sheath 2011 having attached at its own distal periphery a hollow toroidal structure 2014. The hollow toroidal structure 2014 contains the chemical agent or amplifying agent, for example, acetic acid at a 3% to 5% concentration. A retractor 2012 compresses the toroidal structure 2014 when the operator is ready to apply the amplifying agent to the target tissue. When the retractor 2012 is retracted using a trigger like mechanism 2015 the toroidal structure 2014 is compressed and its content is sprayed onto the tissue. Simultaneously with the retraction action, the probe is signaled to start taking measurements, by the actuation of a switch 2016 in the handle of the probe. The chemical or amplifying agent is sprayed through a plurality of perforations 2017 as shown in FIG. 18B, a top view of the distal end of the assembled sheath/retractor assembly. To prevent accidental expulsion of the solution, a covering such as an adhesive tape may be attached to the distal end 2013, covering the toroidal structure 2014. In one embodiment, the covering may be removed after mounting the sheath on the probe and just prior to the insertion of the probe into a target area such as the vagina. While FIG. 18A depicts a cylindrical structure, it should be apparent to those of ordinary skill in the art that a conical structure can be utilized to improve packaging and nesting of multiple disposable sheaths, and furthermore, that any other structure may be constructed which is adapted for the functions depicted in FIG. 18A and which is further adapted for the anatomic region in which it will be used.

In the embodiment shown in FIGS. 18B and 18C, the retractor 2012 is designed to leave an optical window 2018 for the reception of responses from the illuminated tissue. Illumination is achieved through circumferentially distributed optical fibers, as previously described in FIG. 11, and the light is transmitted through a transparent part of the peripheral distal end of the retractor 2012. The toroidal container 2014 for the amplifying agent is affixed to the sheath 2011, as shown in FIG. 18C, which shows a cross sectional view of the distal end of the sheath/retractor assembly. The toroidal container 2014 is directly attached to the sheath (as shown at 2019) or it is affixed in any other suitable way.

While in FIG. 18A we show a toroidal container 2014 which discharges its content upon compression, it should be clear that other shapes may be useful in the practice of the invention. For instance, the cross section of the toroidal container 2014 can be oval or rectangular. In certain embodiments, the amplifying agent container is constructed as a side mounted syringe having a plunger that causes discharge of the amplifying agent in a spray form, while providing simultaneously a signal to the probe that amplifying agent is applied, and thus providing a starting point for the temporal measurements of reflections from the target tissue. While this figure shows one embodiment of a system for automating the application of the amplifying agent and for standardizing the time lapse between the application of the amplifying agent and the measurement of back scattered responses from the target tissue, it should be evident to a person trained in the art that other mechanisms achieving the same goal can be devised without deviating from the spirit of the invention. Such other applicators could include, but are not limited to, surgical applicators like sponges, cloths or swabs that are made to be retracted after the application of the amplifying solution so leave open the optical path between the tissue and the probe's distal end 2013.

When the algorithms use normalized responses, as normalized against time zero, the trigger actuates a timer within the probe controller that sets up a predetermined time interval for the first measurement (typically within 1 second of amplifying agent application). When the algorithm used normalizes responses relative to the response obtained prior to the application of the amplifying agent, an image of the cervix is taken prior to the application and recorded with the frame grabber in the data processing unit 1704. After the trigger 2016 signals the probe to start taking responses, the responses are taken and normalized (pixel by pixel) and one of the algorithms described above analyzes the data. The data are presented as either a "positive" or "negative" finding for the whole cervix, or alternatively, an artificial image of the pathology is presented for those pixels where the algorithms returned positive findings. This image is superimposed on a visual image of the cervix and recorded to allow post screening accurate location of tissue requiring subsequent biopsy.

In some embodiments of the invention, spatial data are averaged over groups of neighboring pixels (between 2×2 to 6×6), and these averages (both for the standardizing measurement, or normalizing measurement) are used as normalized intensities. Other methods for averaging or normalizing spatial data can be used. Different methods of normalizing can be related to the resolution of the CCD used in that specific interest.

In another embodiment, a plurality of chemical agents are applied to a specimen, either simultaneously or sequentially. The use of multiple chemical agents causes any of a number of different effects. One chemical agent is used to control or change pH (e.g., hydrogen ion concentration), change the concentration of one or more other ionic species, or change an osmotic pressure, while another chemical agent is used to induce another sort of change, for example, staining a material, activating or passivating a material, or otherwise changing a physical property of a material.

Application of an exogenous contrast agent when combined with the activation of an endogenous contrast agent gives rise to a combined contrast that provides more valuable information than either agent alone. For example, application of acetic acid to epithelial tissue results in time-dependent effects in the fluorescence emission spectrum resulting from activation of endogenous native fluorophores in tissue, such as NADH, collagen, elastin, favins (e.g., FAD) or porphyrins.

Figure 19:
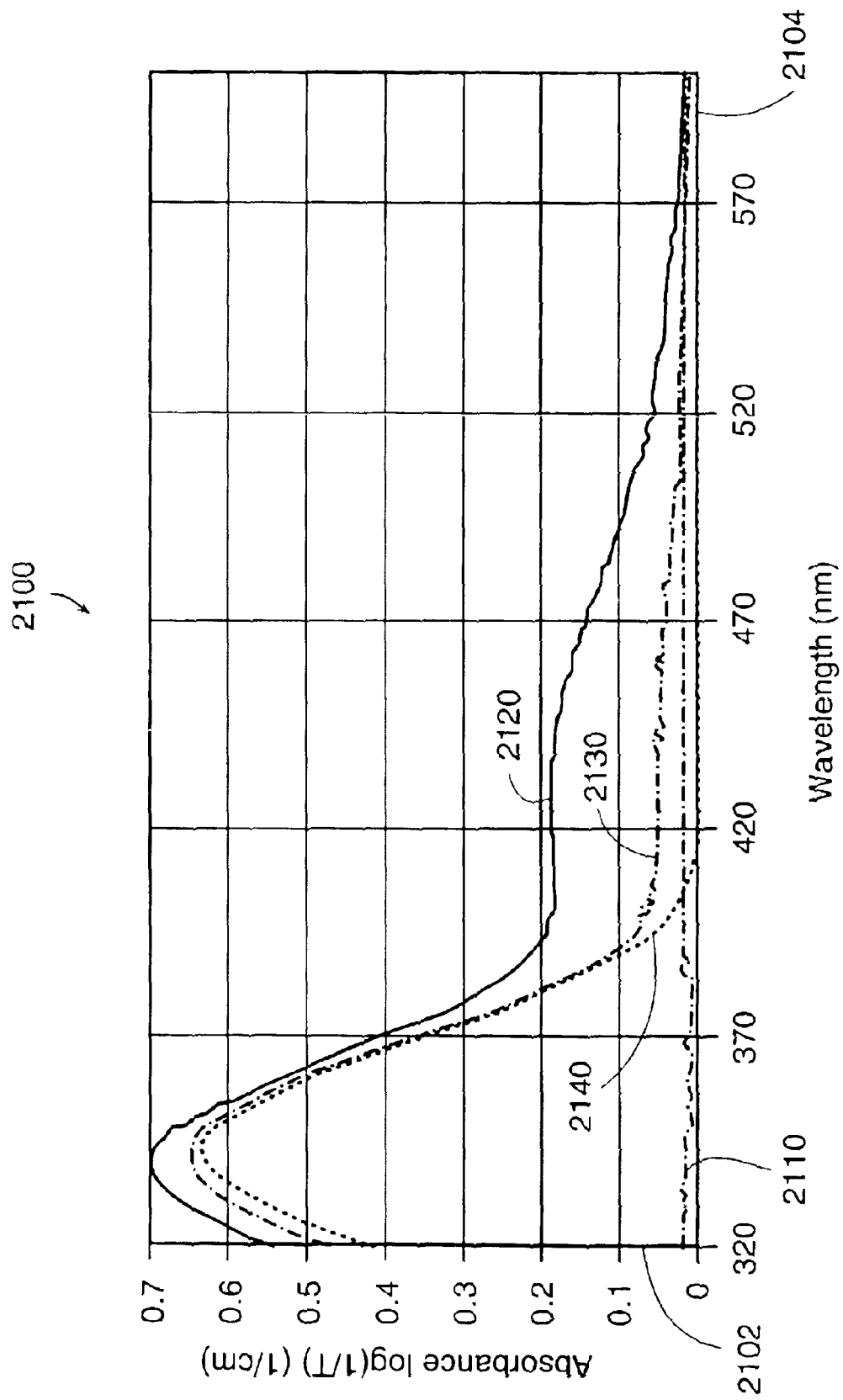
FIG. 19 is a graph of absorption spectra recorded for NADH using a chemical agent according to the invention.

This effect arises from at least two different sources. One source is the penetration of the acetic acid into the tissue followed by the resulting pH change on the spectral properties of the endogenous fluorophore. The effect of pH is shown for NADH in FIG. 19. FIG. 19 shows four absorption spectra recorded over the wavelength range of about 320 nm to aboout 600 nm. The absorbance is plotted along the vertical axis 2102 and the wavelength in nm is plotted along the horizontal axis 2104. A baseline spectrum 2110 is taken for a 5% acetic acid solution containing no NADH, and shows little absorption. The spectrum 2120 is taken at pH 4.0 and shows two strong absorption peaks at approximately 350 nm and at approximately 430 nm. The spectrum 2130 is taken at pH 5.0 and shows a strong absorption peak at approximately 350 nm and a much weaker absorption peak at approximately 430 nm as compared to the pH 4.0 spectrum. The spectrum 2140 is taken at pH 7.0 and shows a strong absorption peak at approximately 350 nm and virtually no absorption peak at approximately 430 nm as compared to the pH 4.0 spectrum. The spectral properties of NADH absorption are significantly affected by pH. Since absorption is the first step in fluorescence, it is reasonable to expect that pH will affect the emitted fluorescence as well.

Acetic acid penetrates into different types of tissues and cells at different rates depending on the type of tissue present. In addition, the amount of NADH in cells typically differs according to the type of cell and its metabolic state. Consequently the kinetics of this pH response can be indicative of the tissue or cell type and its metabolic condition.

Acetic acid causes acetowhitening when applied to certain tissues, such as epithelial surfaces. The acetowhitening effect is produced by light scattering changes. These changes have further secondary effects on spectral measurements, such as induced fluorescence. Changes in the induced fluorescence result from either of two sources. One source is the direct effect of acetowhitening on the penetration of the UV excitation light. A second effect results from the light scattering on the observed spectral shape of the emitted fluorescence. Since the acetowhitening is time dependent, these secondary effects are time dependent as well.

Figure 20:
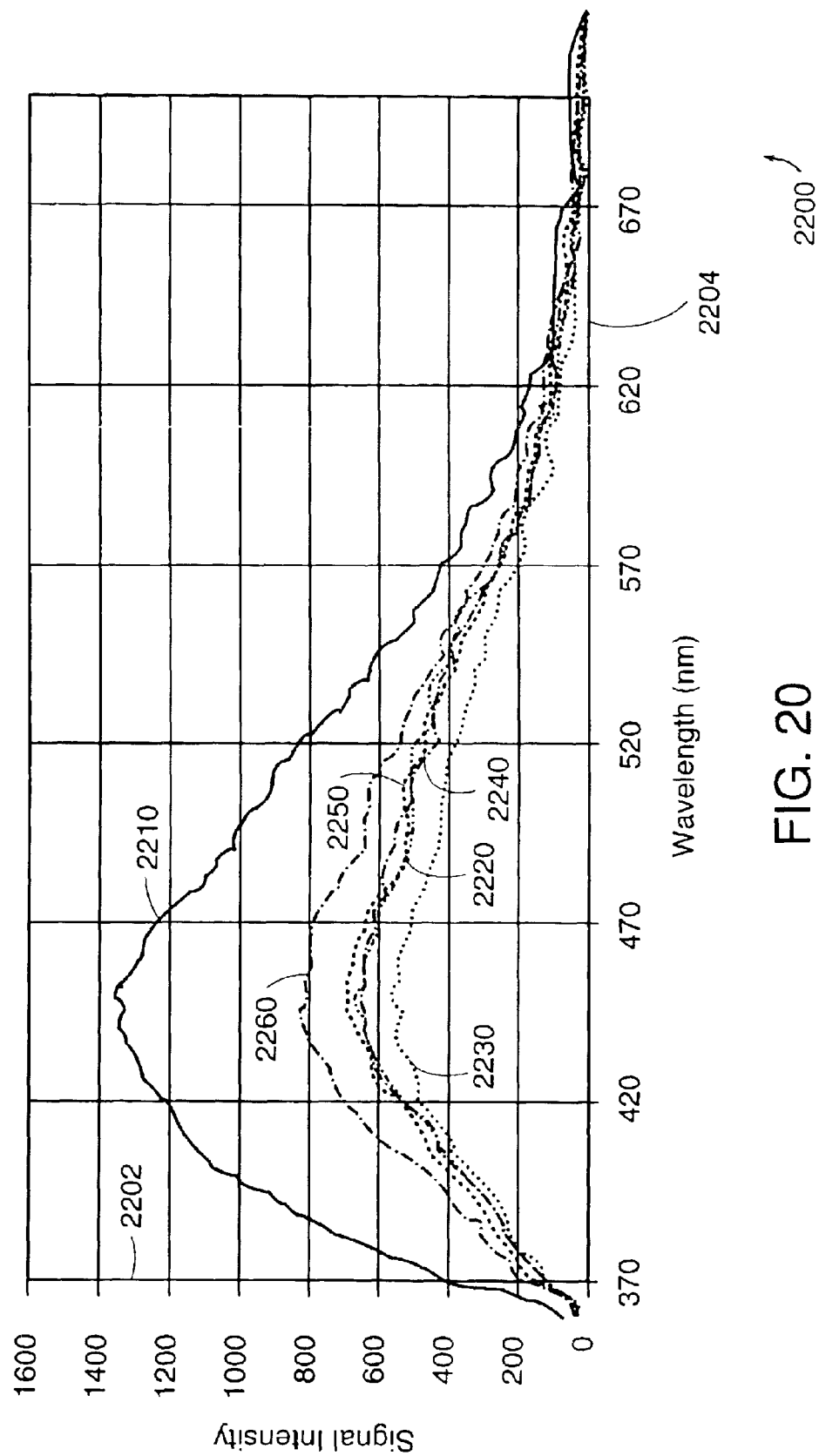
FIG. 20 is a graph of fluorescence spectra as a function of time for specimens treated with a chemical agent according to principles of the invention.

Temporal changes observed in fluorescence emission following the application of acetic acid to a cell suspension is shown in FIG. 20. FIG. 20 shows a graph 2200 of spectra measured as a function of time after application of acetic acid. The spectral intensity is plotted along the vertical axis 2202 and the wavelength in nm is plotted along the horizontal axis 2204. Curve 2210 is recorded at the time of application of the acetic acid solution. Curve 2220 is measured 0.5 minutes after acetic acid application. Curves 2230, 2240, 2250 and 2260 are recorded 1, 2, 3, and 7 minutes after acetic acid application, respectively. The fluorescence spectrum originally observed at the time of acetic acid application quickly decreases in intensity, and recovers slowly thereafter.

Figure 21:
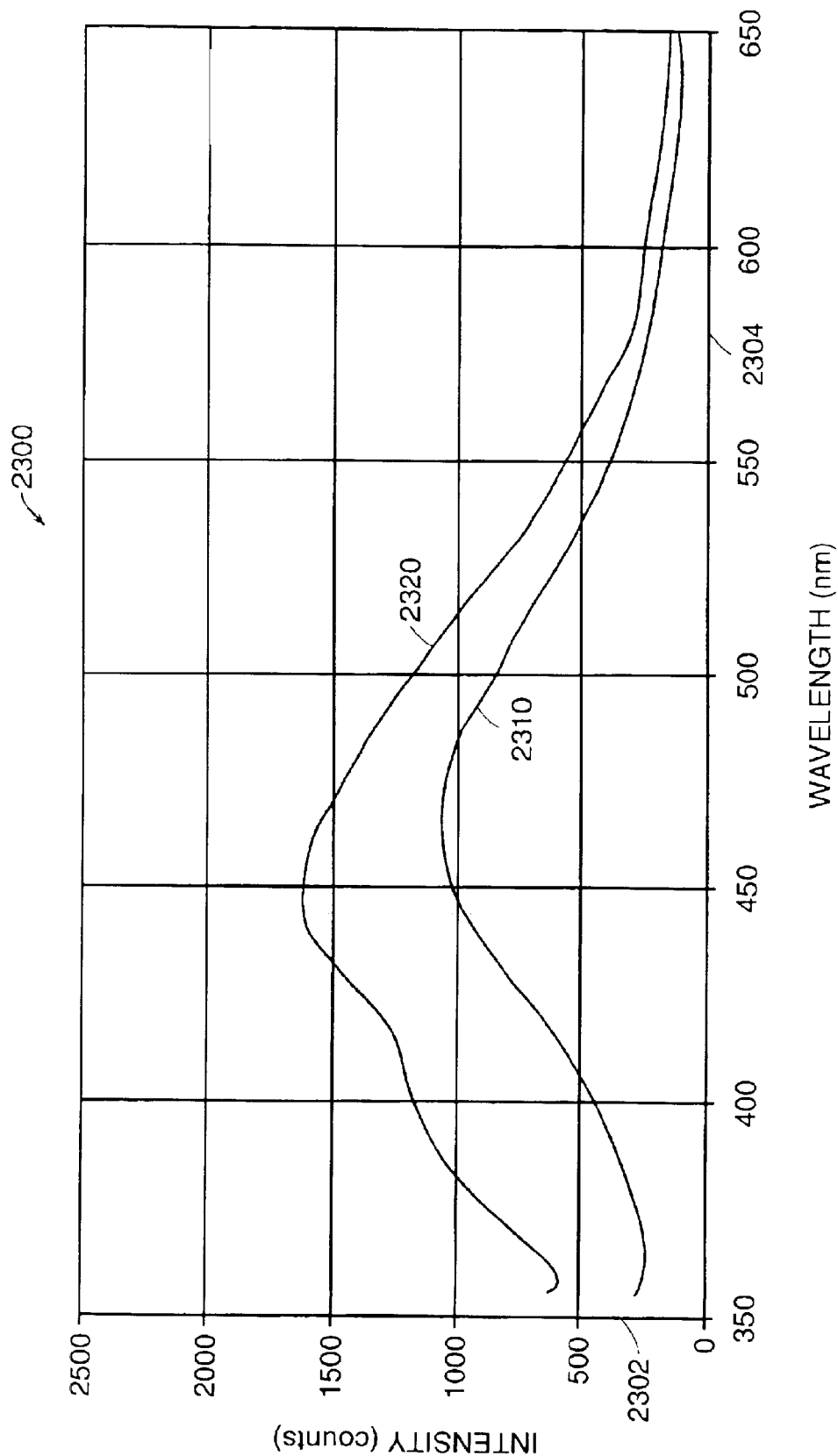
FIG. 21 is a graph of flourescence spectra recorded before and after treatment of a specimen with a chemical agent, according to principles of the invention.

Fluorescence spectra in cervical tissue have similar changes over time following application of acetic acid. FIG. 21 is a graph 2300 that shows the changes in fluorescence spectra before (curve 2310) and after (curve 2320) application of acetic acid to cervical tissue. The spectral intensity is plotted along the vertical axis 2302 and the wavelength in nm is plotted along the horizontal axis 2304. Note that the fluorescent intensity at some wavelengths below about 450 nm changes more substantially than the intensity at wavelengths above about 450 nm. Since the time-course of those changes is related to the type of tissue being probed (as described above) these spectral differences can differentiate the type of tissue under study.

Relative motion between the patient and the colposcope can cause problems with registration of the different images for that patient during analysis. A robust motion detection and correction technique is disclosed below. This technique uses the cross-correlation of two successive images to determine global motion. The cross-correlation is computed in the Fourier domain using a fast Fourier transform. In one embodiment, the image registration technique is used after the specimen data is collected. In an alternative embodiment, systems according to the invention incorporate the technique on-line, as it does not require excessive processing overhead.

Image processing is used to extract relevant features from the data observed and recorded using the systems and methods of the invention. Image processing techniques that can be applied include, but are not limited to, color space transformations, filtering, artifact detection and removal, image enhancement, extraction of three-dimensional shape information, manipulations using mathematical morphology, and segmentation.

A color space transfromation is intended to transform the three primary colors, red (R), blue (B), and green (G), into a new set of colors or values using a kinear or non-linear transformation. A number of well-known transformations interconvert R, G, B and luminance/chrominance components, for example, as used in converting light recorded in a camera into broadcast signals, and rendering broadcast signals on a television display.

Filtering is useful in image processing, and is used to suppress noise and unwanted interfereing signals. Many filters and filtering processes are known. Filters can include both hardware filters such as optical filters and electronic filters, as well as filters applied in software, such as digital filters. For example, the median filter replaces every pixel of an image with the median value computed in a given neighborhood of the pixel.

Artifact detection and removal is used to eliminate spurious information from a set of data to be analyzed. Some artifacts, such as portions of an optical field of view that are extraneous, may be eliminated by changing the height and or width of the field of view, or by masking portions of the field of view, for example when a physician observes that the field of view includes material that is not of interest.

Image enhancement can include processing to improve the visual contrast between adjacent portions of an image. A number of known techniques are available, including applying a weighting function to a range of intensities or gray scale values.

Extraction of three-dimensional shape information is useful in representing a surface that is non-planar in two-dimensions. An example is computing the three-dimensional features of the cervix to account for the nonuniformities of illuminating a three-dimensional surface.

Manipulations using mathematical morphology are well-known. Image processing using the principles of mathematical morphology provides a representation of an image in a form that simplifies the computational burden in image processing.

Morphological operators are based on the mathematics of set theory. A set in mathematical morphology represents the shape of an object in an image . In the case of two-dimensional (binary) images, the sets are members of $Z^2$ and each element represents the (x,y) coordinates of a black (or white, depending on the convention) pixel in the image. Gray-scale, color, time-varying components, or any vector-valued information can be included by extending the Euclidean space size.

The basic morphological operators are described in terms of gray-scale images below. Let the input image be described by a function $f:Z^2 \to R$. Gray-scale dilation is defined as:

$$(f \oplus b)(v, w) = \max\{f(v-x, w-y) + b(x, y) | (v-x, w-y) \in D_f; (x, y) \in D_b\}$$

where $b: Z^2 \to R$ is a function called a structuring element, $D_f$ is the domain of $f$ and $D_6$ is the domain of b. The structuring element has a key role in this operator: it is added morphologically to the image at each pixel location.

The opposite of dilation is erosion. The erosion operator is defined as:

$$(f \ominus b)(v, w) = \min\{f(v+x, w+y) - b(x, y) | (v+x, w+y) \in D_f; (x, y) \in D_b\}$$

In this case the structuring element is subtracted morphologically from the image at each pixel location.

Two important morphological operators are defined using erosion and dilation: opening and closing. They are respectively defined as:

$$f \circ b = (f \ominus b) \oplus b$$

$$f \cdot b = (f \oplus b) \ominus b.$$

The effect of opening is to preserve holes and remove peaks, while closing preserves peaks and closes holes according to the structuring element's shape. The structuring element b is fitted from inside (below an image) in the opening case and fitted from outside (above an image) in the closing case.

A morphological filter can be defined as any combination of morphological operators. For example $(f \circ b) \cdot b$, opening followed by closing, or $(f \cdot b) \circ b$, closing followed by opening. These operators are neither commutative, nor associative or distributive and the filtering operators cited above are not equal. One of the following two filters is used:

$$f\_b = \frac{1}{2}[(f \cdot b) + (f \circ b)],$$

and $$f\_b = \frac{1}{2}[(f \circ b) \cdot b + (f \cdot b) \circ b]$$

where the _ symbol means $f$ filtered by b.

A more elegant way to achieve a morphological filtering with better geometrical characteristics is to use geodesic reconstruction after a morphological opening. The reconstruction process uses geodesic dilation which for gray-scale images is defined by:

$$(f \oplus b)^{(1)}(v, w) = \min\{(f \oplus b)(v, w), f_0(v, w)\}, (v, w) \in D_f,$$

where $f_0$ is the reference image, usually the original image, and g is a small structuring element, usually a four pixel (cross) or eight pixel (square) connected element. Geodesic reconstruction is obtained by repeating the geodesic dilation n times $((f \oplus b)^{(n)})$ until idempotency is reached. The geodesic reconstruction is then written:

$$Rg = (f \oplus b)^{(i)}, \text{ with } (f \oplus b)^{(i+1)} = (f \oplus b)^{(i)}$$

An equivalent operator can be defined for reconstruction after morphological closing which uses geodesic erosion. For gray-scale images it is defined as:

$$(f\_b)^{(1)}(v, w) = \max\{(f\_b)(v, w), f_0(v, w)\}, (v, w) \in D_f$$

An example of geodesic reconstruction after morphological opening suppresses the square shape deformation introduced by the opening process. These geodesic reconstruction operators significantly improve any filtering process for a modest additional computation time.

The most natural example of diffusion process is heat transfer inside matter. This physical phenomenon is mathematically expressed by the following partial differential equations:

$$q = -k \nabla T,$$

$$cp \frac{\partial T}{\partial t} = -\nabla \cdot q + f,$$

leading to the following second order elliptic equation:

$$cp \frac{\partial T}{\partial t} = -\nabla \cdot (k \nabla T) + f,$$

Heat transfer involves a thermal flux q. The whole system must obey the law of energy conservation. The symbol $\nabla$ is the differential operator, which is defined as $\nabla = (\partial|\partial x_1, \ldots, \partial|\partial x_d)$. The parameter p is the density of the medium, k is the thermal conductivity, c is the specific heat capacity, and $f$ the capacity of internal heat sources. An analogy exists between temperature variation and value variation in images. The basic formulation is obtained when the medium is assumed to be homogeneous, without sources and with constant conductivity.

In image processing applications the ideal objective is to obtain an image where only strong edges are preserved while noise and small structures are smoothed out. Diffusion is used as an edge preserving filtering method. The thermal conductivity is replaced by a conductivity function which adapts the diffusion to the local gradient: decreasing diffusion for increasing gradient. The above diffusion equation becomes:

$$\frac{\partial v}{\partial t} = \nabla \cdot (D \nabla u),$$

where v(x,t) is the signal value at time t and position x, and D is a conductivity matrix. The latter defines the type of diffusion:
- if D reduces to a constant value k then the diffusion is isotropic,
- if D reduces to a nonlinear function g(·) then the diffusion is nonlinear isotropic,
- if D is a tensor whose elements are functions gij (·) then the diffusion is anisotropic.

The analysis uses the case where D=g(·), and the following conductivity function:

$$g(|\nabla v|) = \begin{cases} 1 & \text{if } |\nabla v| \leq k_o \\ k_o/|\nabla v| & \text{if } |\nabla v| > k_o \end{cases},$$

$$\Phi f(|\nabla v|) = \begin{cases} 1 & \text{if } |\nabla v| \leq k_o \\ 0 & \text{if } |\nabla v| > k_o \end{cases},$$

Histogram equalization re-assigns pixel values in order to obtain a uniform distribution. Let v(x) be the pixel value at location x and P(v) be the probability density function associated to v. The following transformation is used:

$$v_{eq}(v) = \int P(s) ds$$

where $0 \leq v \leq 1$. In the discrete case, the uniform distribution is only approximated and the following equation is used:

$$u_{k,eq} = \sum_{j=0}^{k} \frac{n_l}{n},$$

where n is the total number of pixels and $n_j$ the number of pixels with value equal to j.

The fitting technique used is called linear least squares. The idea is to fit a linear combination of arbitrary functions (linear or nonlinear) given by:

$$l(x) = \sum_{k=0}^{M-1} \alpha_k f_k(x),$$

where x is an N-dimensional coordinate vector (N=2 in the case of images), to a set of data $l_i(x_j)$, with i=0, ..., n−1. In one embodiment, the following series of functions are used:

$$1, x, x^2, x^3, \ldots,$$

in the 1-D case and:

$$1, x, y, x^2, xy, y^2, x^3, x^2y, xy^2, y^3, \ldots,$$

in the 2-D case.

The fitting criteria is the minimization of the following least-square error:

$$x^2 = \sum_{i=0}^{n-1} \left[ \frac{l_i - \sum_{K=0}^{M-1} \alpha_k f_k(x_i)}{\sigma_i} \right]^2$$

where $\sigma_1$ is the measurement variance at location $x_1$. In one embodiment, set $\sigma_1$=1, $\forall$ i=1, ..., n−1.

By defining the n×M matrix A whose elements $A_{ij}$ are given by:

$$A_{ij} = f_j(x_i),$$

and the vector b of length n whose elements $b_i$ are given by $b_i = l_i$, then the following system must be solved:

$$a = (A^T A)^{-1} A^T \cdot b,$$

where $a = [\sigma_0 \ldots \sigma_{m-1}]$. Since the $A^T A$ product is positive definite, Cholesky decomposition can be used to compute the inverse.

Segmentation is a morphological technique that splits an image into different regions according to a pre-defined criterion. In the analysis of the state of health of a biological specimen, it is meaningful to compare the proprties of different areas of the specimen. Segmentation is a method that directly provides information on how many regions are present in the image of a specimen, and the location of each region.

In one embodiment, colposcopic images are segmented to track regions in a time series of images. Relevant features are extracted from the labeled regions and their evolution is analyzed as a function of time, to measure and localize acetowhitening effects. Colposcopic images are segmented using a watershed based algorithm. An efficient pre-processing scheme is used, as are two region merging techniques. The use of markers to track the segmentation in time-series of images is used, and the problem of global motion and local deformations related to the precise tracking of these markers is discussed.

A segmentation scheme for colposcopic images separates the image of the cervix into a number of regions according to an intensity criterion. Segmentation techniques are well known in the mathematical morphology arts. In one embodiment, the object (e.g., the cervix) is known and multiple regions with different intensity content within the cervix are to be identified.

Figure 22:
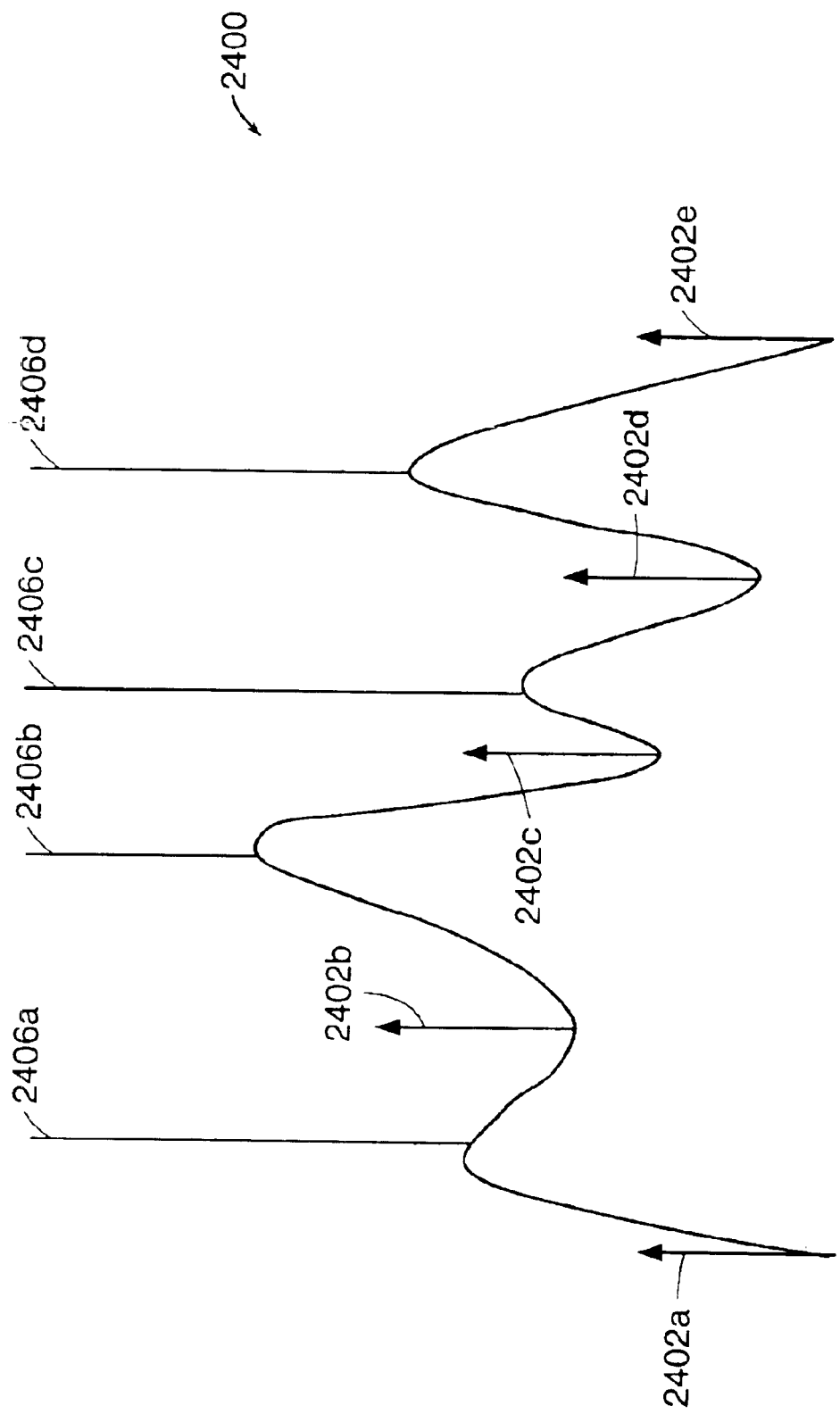
FIG. 22 is a one-dimensional diagram of watershed segmentation.

A technique based on the structural and spatial information rather than on the spectral information is suited to analyze colposcopic images. One approach uses the watershed technique. The watershed technique uses structural information. The watershed technique provides a fine to coarse segmentation of an image in combination with region merging techniques. The flooding technique views a gray-level image as a 3-dimensional surface and progressively floods this surface from below. Each local minimum in the surface is thought of as a hole. A rising water level floods a region as soon as a hypothetical water level reaches the associated minimum. FIG. 22 illustrates this concept on a 1-D signal. The arrows 2402a–2402d show the flooding origins and directions and the solid lines 2406a–2406d are the watersheds. The flooded minima are called catchment basins and the borders between neighboring basins are called watersheds. Only the catchment basins are of interest. They constitute the segmented image. Fast implementations use first-in-first-out (FIFO) queues and sorted data.

Figure 23:
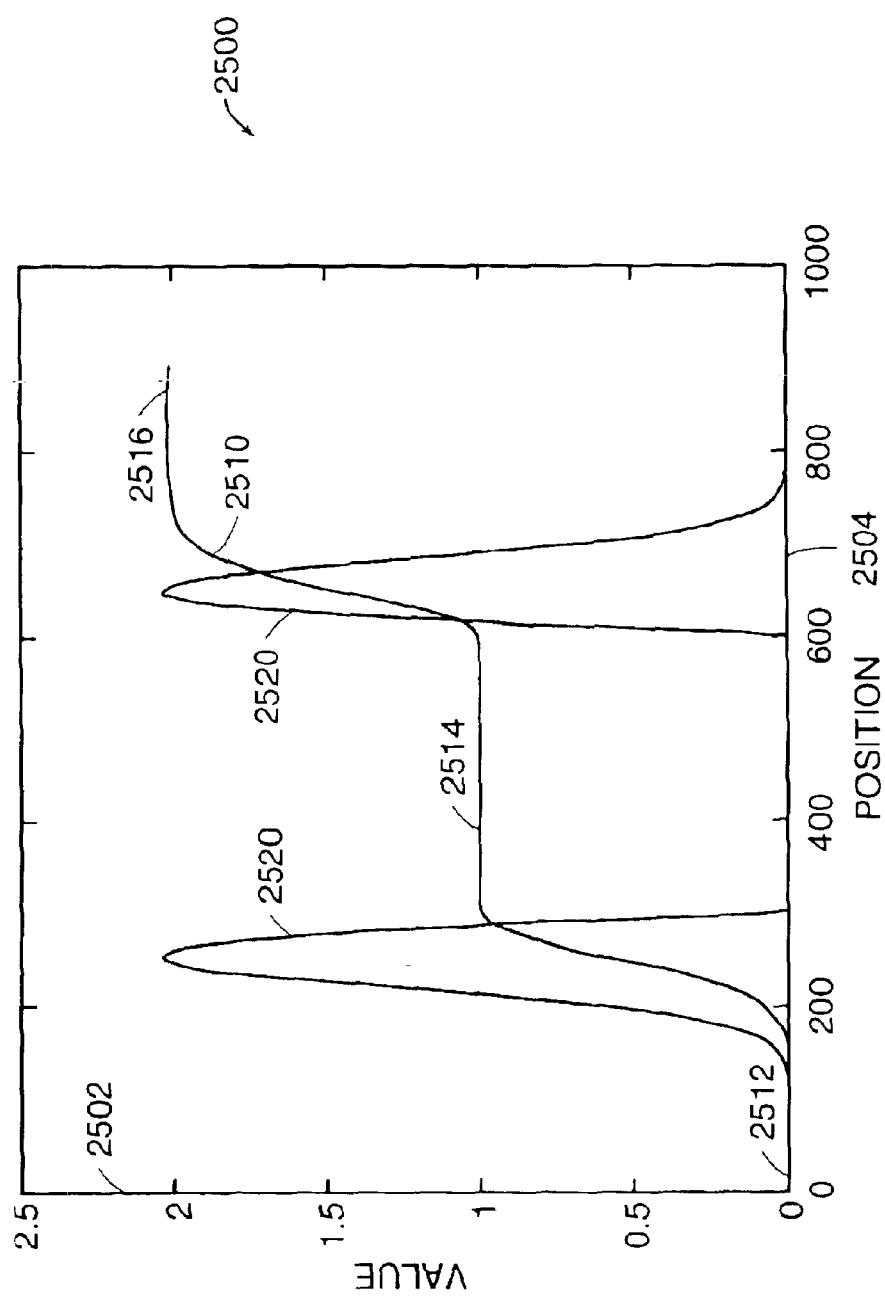
FIG. 23 is a graph of a signal and its first derivative.

FIG. 23 is a graph 2500 of a signal 2510 and its first derivative 2520, both plotted with amplitude as a vertical axis 2502 and position as a horizontal axis 2504. FIG. 23 shows a signal 2510 used to represent watersheds with three distinct regions (hole 2512, plateau 2514, and peak 2516) and its derivative function 2520, or gradient. Image segmentation with the watershed transform is performed on the image gradient 2520. The signal shows three distinct regions, and the direct watershed transform would produce a one lowest region. The gradient 2520 separates the signal into its three regions. An analogous principle holds for two-dimensional signals, i.e. images.

Figure 24:
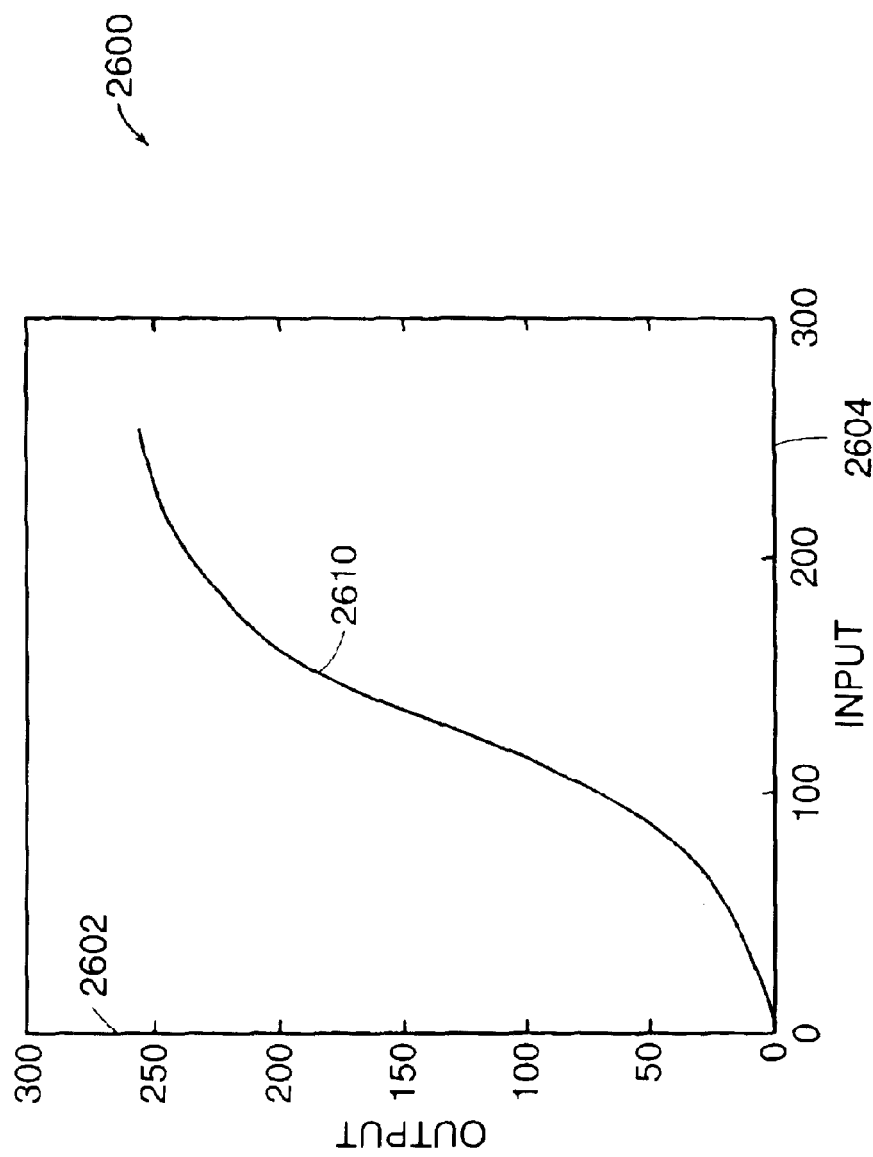
FIG. 24 shows a sigmoidal scaling function used to enhance the contrast between light and dark regions of an image.

FIG. 24 shows a graph 2600 of a sigmoidal scaling function 2610 used to enhance the contrast between light and dark regions of an image. The sigmoidal scaling function 2610 is plotted as output along a vertical axis 2602 as a function of an input that is indiated along a horizontal axis 2604. The use of the watershed transform often leads to a severe over-segmentation. Pre-processing is performed to reduce the number of regions in a segmented image. In one embodiment, a pre-processing scheme reduces the number of regions from several thousand to several hundreds:

An algorithm that treats images to provide a segmented image includes the following steps:
computing luminance component L*;
performing 3-D shape compensation;
performing sigmoidal scaling;
morphological closing/opening with a cylindrical structural element;
performing geodesic reconstruction;
computing image gradient;
computing threshold gradient;
performing closing; and
performing geodesic reconstruction of the gradient image.

The uniform luminance component L* is well adapted to the segmentation process, and is computed for an image of interest.

3-D shape compensation removes an artifact (e.g., a stair-case effect) in the segmented image. The illumination is non-uniform when falling on a curved surface (e.g., the cervix), which in turn influences the gradient values used for the segmentation.

A sigmoidal scaling function is used to improve the contrast between light and dark regions. FIG. 24 is a graph of a scaled sigmoid, used in this study. The sigmoid increases contrast in the median intensity range by providing a larger number of quantification levels. Applying a sigmoidal scaling function causes dark and very light areas to exhibit diminished contract, while the limit between light and dark regions is enhanced.

Closing and opening morphological operators, respectively, are used to suppress small regions corresponding to holes or peaks in the images. The geodesic reconstruction keeps the geometrical aspect of the image as close as possible to that of the original image. A morphological closing with geodesic reconstruction is performed on the gradient of the filtered image to remove plateaus, which are visualized as separate regions in the watershed transform. The diameter of the cylinder used as structuring element defines the minimum size of the regions in the segmented image.

Finite-element approximations are used to compute derivatives. Alternative approaches involve using a Sobel operator, which is a 3×3filter. Another alternative is the use of a local cubic polynomial approximation, which is a 5×5 filter. Before processing the gradient for the watershed extraction, application of a threshold removes small values.

In one embodiment, the gradient is computed using cubic mean-square approximation. In another embodiment, a morphological closing/opening filter with geodesic reconstruction is first applied and then the gradient is computed. Spurious regions are smoothed out and contrast enhanced in large regions by both methods.

In one embodiment, the watershed algorithm is modified as follows. The data is represented in floating point, and the interval steps between successive flooded levels is not uniform. Also, each watershed pixel is merged into a neighboring region according to a nearest neighbor criterion.

The region merging step following the watershed transform step reduces over-segmentation. In one embodiment, neighboring regions are merged if an intensity change along their border is greater than a given threshold. Alternatively, neighboring regions are merged if a difference in mean intensity value is greater than a given threshold.

In both embodiments, a map of all border pixels is used. For each segment, a computer computes the difference between the mean value of pixels of each of the two regions under consideration. If the absolute value is below a given value, the segment is removed from the mask, and the regions are merged. The final mask is used to map out the gradient image. The watersheds are recomputed.

An alternative merging algorithm uses the same routines. The alternative algorithm uses the mean value image as input in place of the original image. Since all pixels in a region have the same (mean) value, the algorithm works differently, in that border segments are suppressed if the difference in mean value between neighboring regions is smaller than a given threshold. A morphological distance is an approximation of the distance, in pixels, from a pixel to the nearest segment border. A method to use markers to track the segmentation in time series of images is now presented. The extraction of markers is necessary in order to initialize the flooding process in the watershed transform computed in successive images (e.g., in time-series).

The approach used comprises the steps of finding pixels having minimum value for each region, and selecting the minimum with the largest morphological distance for each region.

The first step selects the minimum value as an initial marker, since the flooding used in the watersheds start at local minima. The pixel with minimum value and largest morphological distance is used to avoid a small deformation of a region pushing a marker outside of the region.

A homotopy modification of the gradient image obtained with the markers is used to suppress catchment basins corresponding to minima that have not been marked, in order to speed up the computation. The homotopy modification of v is the geodesic reconstruction of v (mask) from $\acute{v}$ (marker).

$$\tilde{v}(\kappa, i) = \begin{cases} v(\kappa, i) & \text{if } (\kappa, i) \in M \\ \max_y v(\kappa, i) & \text{otherwise.} \end{cases}$$

In one embodiment, more than one marker per region is considered. Pixels having a morphological distance greater than a given value (typically 2–3) or being at least equal to the largest morphological distance within a given region are considered. These markers are used to zero out gradient values in the following image, in order to reduce influence of local maxima on the homotopy modification. It is assumed that the borders between neighboring regions are located somewhere between the marked regions.

Further, the markers are used to initialize the watershed algorithm with the gradient image of the next image. Tracking schemes are employed to take into account global and local motion.

One illustrative tracking scheme for the detection of patient motion during an acquisition cycle uses the cross-correlation of two sub-images of two successive images to determine the global motion. An alternative algorithm is used to track motion for segmentation tasks.

Typically, images of specimens exhibit large homogeneous regions which are difficult to track. Structural information is used to improve motion tracking. Derivatives are used instead of the original image. Using the gradient improves the system's sensitivity to glare, while the use of the sum of the gradients in both the x and y directions highlights low-contrast structures. Using the Laplacian operator (the sum of second derivatives) provides similar results. Applying a low-pass filter before computing the derivatives yields results similar to the Laplacian of Gaussian used for edge detection. The low pass filter suppresses noise and smoothes out glare.

The embodiment further comprises three modifications. The true cross-correlation of successive images is computed in a 512×512 pixels window. The two windows used for each image are different and are of sizes 302×302 and 210×210, respectively. A Hamming window is used to extract these two signals. The two windows have different sizes to make sure that the second signal is completely contained in the first one, and the use of a Hamming window avoids small oscillations, especially at the transition of the selected signals and the zero-padded areas. The equations used for the motion detection are given below.

Optical flow algorithms are used to measure local motions. In order to save computation time, the optical flow is computed only for the markers. Optical flow is defined as the distribution of apparent velocities of movement of brightness patterns in an image, and is used to reconstruct three-dimensional surfaces in medical imaging applications.

Additional embodiments of motion detection algorithms include the following steps: implementation of a local deformation tracking system for improving the precision of marker tracking; extraction of feature signals from the series of segmentation results; analysis of feature signals and classification into groups of interest; and use of group information to correlate the evolution with the histology.

For motion detection, only a single frame is used. The three RGB color components are transformed into a single intensity component using the following relationship:

$$I = 0.299 \cdot R + 0.587 \cdot G + 0.114 \cdot B$$

In order to suppress high-frequencies due to noise and to the interlaced video signals, we apply a Gaussian low-pass filter to the intensity component:

$$g(\vec{x}) = \frac{1}{\sqrt{2\pi\sigma^2}} \exp\left(\frac{(\vec{x}-\vec{\mu})^T \cdot (\vec{x}-\vec{\mu})}{2\sigma^2}\right)$$

where $\vec{\mu}$ is the center (mean value) of the Gaussian and $\sigma$ is its standard deviation. Finally, we use only derivative information to compute the translation parameters, either the sum of derivatives $$\frac{\partial}{\partial x} + \frac{\partial}{\partial y}$$

or the Laplacian $$\frac{\partial^2}{\partial x^2} + \frac{\partial^2}{\partial y^2}.$$

Motion can be detected using a cross-correlation operator applied to two successive images in a sequence.

The cross-correlation is computed in the Fourier domain using a fast Fourier transform. The following relationship is used:

$$\Phi = X \cdot Y^*$$

where $\Phi$, X, and Y are the Fourier transform of the cross-correlation function, the first, and the second signal, respectively. The * symbol represents the complex conjugate. Note that the cross-correlation of two signals of length $N_1$ and $N_2$ provides $N_1 + N_2 - 1$ values and therefore, in order to avoid aliasing problems due to under-sampling, the two signals must be padded with zeros up to $N_1 + N_2 - 1$ samples.

For discrete signals (i.e. sampled and quantized signals), the discrete Fourier transform (DFT) and the inverse discrete Fourier transform (IDFT) are given respectively by:

$$v(k, l) = \sum_{m=0}^{N-1} \sum_{n=0}^{M-1} u(m, n) \exp\left(-\frac{j2\pi mk}{N}\right) \exp\left(-\frac{j2\pi nl}{M}\right)$$

$$u(m, n) = \frac{1}{NM} \sum_{k=0}^{N-1} \sum_{l=0}^{M-1} v(m, n) \exp\left(\frac{j2\pi mk}{N}\right) \exp\left(\frac{j2\pi nl}{M}\right)$$

This transform expands the signal onto an orthonormal basis of exponential functions. Once the inverse discrete transform is computed, the location of the maximum value corresponds to the translation necessary to align both images.

Different types of windows are used for spectral analysis, when only part of a signal is analyzed. The goal is to avoid oscillation around discontinuities (Gibbs phenomenon). A Hamming window can be used, which is given by the following relationship:

$$\omega_h(k) = \tfrac{1}{2}[1 + \cos(2\pi k/N)]$$

where N is the number of samples, k is the sample index, and $-N/2 \leq k \leq -N/2$. In the frequency domain, the Fourier transform of the signal is convolved with the Fourier transform of the Hamming window. For the two-dimensional case the Hamming window is constructed as a separable function, i.e. $\omega_h(k,l) = \omega_h(k) \cdot \omega_h(k)$, where (k,l) are the pixel coordinates.

As mentioned above, in some embodiments, the cross-correlation of the sum-of-derivatives images is the basis of a motion detection algorithm.

The cross-correlation of two images in a sequence provides information about the translation necessary to obtain the best match in the inner-product sense. However, this does not necessarily mean that the two images are perfectly aligned. A validation method is necessary to measure the "quality" of the matching.

The Sobel operator is given by:

$$fs = \frac{1}{8}\begin{pmatrix} -1 & 0 & 1 \\ -2 & 0 & 2 \\ -1 & 0 & 1 \end{pmatrix}$$

This filter is obtained by convolving the finite element approximation to derivatives with a weight matrix:

$$fs = \frac{1}{2}\begin{pmatrix} 0 & 0 & 0 \\ -1 & 0 & 1 \\ 0 & 0 & 0 \end{pmatrix} ** \frac{1}{4}\begin{pmatrix} 0 & 1 & 0 \\ 0 & 2 & 0 \\ 0 & 1 & 0 \end{pmatrix}$$

where ** is the two-dimensional convolution. The second filter in Equation 2 is a low-pass filter in the direction perpendicular to the derivative operator, which renders the filter less sensitive to noise. The derivative along the y-axis is obtained by using the transposed version of the Sobel operator.

Another way to compute derivatives is to use a local polynomial approximation by minimizing the mean-square error (MSE) with the underlying image pixels. The approximation is given by:

$$v(\kappa, i) \approx \sum_{i=0}^{8} b_i \phi_i(\kappa, i)$$

where (k,l) are the coordinates in the local 5×5 domain centered on the current pixel. The $b_1$ coefficients are the optimal weights in the MSE sense and the $\Phi_1$, are orthogonal polynomials (1, k, l, $k^2 - \tfrac{2}{3}$, $l^2 - \tfrac{2}{3}$, kl, $(k^2 - \tfrac{2}{3})l$, $(l^2 - \tfrac{2}{3})k$, $(k^2 - \tfrac{2}{3})(l^2 - \tfrac{2}{3})$). The minimization of the MSE leads to the following filter for the first derivatives:

$$f\rho = \frac{1}{50}\begin{pmatrix} -2 & -1 & 0 & 1 & 2 \\ -2 & -1 & 0 & 1 & 2 \\ -2 & -1 & 0 & 1 & 2 \\ -2 & -1 & 0 & 1 & 2 \\ -2 & -1 & 0 & 1 & 2 \end{pmatrix} -$$

$$\frac{17}{300}\begin{pmatrix} -1 & 2 & 0 & -2 & 1 \\ -1 & 2 & 0 & -2 & 1 \\ -1 & 2 & 0 & -2 & 1 \\ -1 & 2 & 0 & -2 & 1 \\ -1 & 2 & 0 & -2 & 1 \end{pmatrix} + \frac{1}{144}\begin{pmatrix} 4 & 2 & 0 & -2 & -4 \\ -2 & -1 & 0 & 1 & 2 \\ -4 & -2 & 0 & 2 & 4 \\ -2 & -1 & 0 & 1 & 2 \\ 4 & 2 & 0 & -2 & -4 \end{pmatrix}$$

The center of each image is divided into an 8×8 array of blocks of size 32×32. The array is chosen to avoid the image borders. The borders can contain extraneous material, that is, not part of the cervix. In normal use, the physician attempts to keep the cervix in the middle of the image.

For each of the blocks the normalized inner product with the corresponding block in the adjacent motion compensated image is computed:

$$P_{i,j} = \frac{\sum X \in B_{i,j} I_2(x) \cdot I_2(x)}{\sqrt{\sum \chi \in B_{i,j} I_1^2(x)} \cdot \sqrt{\sum x \in B_{i,j} I_2^2(x)}}$$

where $B_{ij} \subset N^2$ is the domain of definition of block (i,j), and $I_{1,2}$ are the two processed images. The absolute value of $P_{ij}$ is used as a quality measure.

The method is used for series of 28 images and the motion is estimated for each of them, except for the first one. Once the motion parameters are determined, the frame is shifted to its computed "correct" location and the above block-based correlation is computed with the previous shifted image. The result obtained when using the intensity values for each image is plotted with the x-axis corresponding to the different blocks while the y-axis corresponds to the different images. For the example presented above, the shifted images match perfectly and the output is zero intensity everywhere.

In an alternative embodiment, in which edge information is the only information used in the matching correlation, the intensity images are replaced with sum-of-derivatives images. To date, this embodiment has provided less favorable motion compensation than the other embodiment. However, the sum-of derivatives approach appears to provide better identification of sudden or gross motion.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for monitoring effects of a chemical agent on a sample, the method comprising the steps of:

dispensing a chemical agent on a sample;

providing an automated triggering signal to initiate a measurement period relative to said dispensing step;

capturing a plurality of sequential images of said sample during said measurement period;

automatically aligning a subset of said plurality of images to compensate for sample motion; and measuring an optical signal observed from said sample within said measurement period.

2. The method of claim 1, wherein said triggering signal is provided substantially simultaneously with said dispensing step.

3. The method of claim 1, wherein said triggering signal is provided after said dispensing step.

4. The method of claim 1, wherein said measuring step comprises measuring said optical signal at at least one predetermined time relative to said triggering signal.

5. The method of claim 1, wherein said dispensing step comprises dispensing said chemical agent as a mist in a predefined pattern on said tissue.

6. The method of claim 5, wherein said pattern is substantially circular.

7. The method of claim 5, wherein said pattern is substantially annular.

8. The method of claim 5, wherein said mist is a controlled volume.

9. The method of claim 5, wherein said dispensing occurs at a controlled rate.

* * * * *